(12) United States Patent
Robinson et al.

(10) Patent No.: US 10,736,511 B2
(45) Date of Patent: Aug. 11, 2020

(54) METHODS AND APPARATUSES FOR CENTRAL VENOUS PRESSURE MEASUREMENT STATUS

(71) Applicant: Medici Technologies LLC, Albuquerque, NM (US)

(72) Inventors: Mark Ries Robinson, Albuquerque, NM (US); Elena A Allen, Albuquerque, NM (US); Fahimeh Salehpour, Albuquerque, NM (US)

(73) Assignee: Medici Technologies LLC, Albuquerque, NM (US)

( * ) Notice: Subject to any disclaimer, the term of this patent is extended or adjusted under 35 U.S.C. 154(b) by 0 days.

(21) Appl. No.: 16/074,083

(22) PCT Filed: Nov. 17, 2017

(86) PCT No.: PCT/US2017/062366
§ 371 (c)(1),
(2) Date: Jul. 31, 2018

(87) PCT Pub. No.: WO2018/094248
PCT Pub. Date: May 24, 2018

(65) Prior Publication Data
US 2019/0336017 A1    Nov. 7, 2019

Related U.S. Application Data

(60) Provisional application No. 62/423,768, filed on Nov. 17, 2016.

(51) Int. Cl.
*A61B 5/022* (2006.01)
*A61B 5/11* (2006.01)
(Continued)

(52) U.S. Cl.
CPC .......... *A61B 5/0053* (2013.01); *A61B 5/0077* (2013.01); *A61B 5/022* (2013.01);
(Continued)

(58) Field of Classification Search
None
See application file for complete search history.

(56) References Cited

U.S. PATENT DOCUMENTS

| 5,280,789 A * | 1/1994 | Potts .................. A61B 5/02152 33/379 |
| 7,214,193 B2 * | 5/2007 | Freund .................. A61B 5/022 600/490 |

(Continued)

OTHER PUBLICATIONS

Shelley, Kirk H.; Dickstein, Marc; Shulman, Steven M., The detection of peripheral venous pulsation using the pulse oximeter as a plethysmograph, 1993, Journal : Journal of Clinical Monitoring.
(Continued)

*Primary Examiner* — Luther Behringer
(74) *Attorney, Agent, or Firm* — V Gerald Grafe

(57) ABSTRACT

Method and systems are provided for reliable, convenient, self-administered, and cost-effective determination of central venous pressure. The noninvasive method and apparatus use changes in transmural pressure to create detectable changes in peripheral venous vascular volume for the determination of central venous pressure. Transmural pressure changes can be manifested by intravascular or extravascular pressure changes. The system is noninvasive and uses optical measurements of venous volume in the presence of transmural pressure changes. The relationship between the transmural pressure change and the change in vascular venous volume is combined with anatomical measurements to determine the central venous pressure of the subject. Central venous pressure can be used to determine hemody-
(Continued)

namic status of the subject to include fluid overload in the heart failure patient.

25 Claims, 39 Drawing Sheets

(51) Int. Cl.
```
A61B 5/107      (2006.01)
A61B 5/00       (2006.01)
A61B 5/03       (2006.01)
A61B 5/026      (2006.01)
A61B 5/023      (2006.01)
```
(52) U.S. Cl.
CPC ............ *A61B 5/023* (2013.01); *A61B 5/0261* (2013.01); *A61B 5/02233* (2013.01); *A61B 5/03* (2013.01); *A61B 5/1075* (2013.01); *A61B 5/1079* (2013.01); *A61B 5/1114* (2013.01); *A61B 5/683* (2013.01); *A61B 2562/0247* (2013.01)

(56) References Cited

U.S. PATENT DOCUMENTS

| | | | | |
|---|---|---|---|---|
| 7,641,614 | B2* | 1/2010 | Asada | A61B 5/02225 600/485 |
| 2002/0188205 | A1* | 12/2002 | Mills | A61B 5/02028 600/481 |
| 2004/0044290 | A1* | 3/2004 | Ward | A61B 5/022 600/490 |
| 2005/0131306 | A9 | 6/2005 | Mills | |
| 2005/0215912 | A1* | 9/2005 | Freund | A61B 5/022 600/485 |
| 2007/0055163 | A1* | 3/2007 | Asada | A61B 5/02225 600/485 |
| 2007/0239041 | A1 | 10/2007 | Chatterjee | |
| 2008/0183232 | A1 | 7/2008 | Voss | |
| 2011/0077462 | A1* | 3/2011 | Saitou | A61B 1/0638 600/109 |
| 2014/0117256 | A1* | 5/2014 | Mueller | A61B 5/0071 250/459.1 |

OTHER PUBLICATIONS

Yang, Jinfeng; Zhang, Ben; Shi, Yihua, Scattering Removal for Finger-Vein Image Restoration, 2012, Journal : Sensors.
Rowlands, Alex V.; Yates, Thomas; Olds, Tim S.; Davies, Melanie; Khunti, Kamlesh; Edwardson, Charlotte L., Sedentary Sphere: Wrist-Worn Accelerometer-Brand Independent Posture Classification, 2016, Journal : Medicine & Science in Sports & Exercise.
Remmen, Johannes Jacobus, Non-invasive assessment of pulmonary capillary wedge pressure in the elderly by the Valsalva manoeuvre, 2006, Thesis: s.n.].
Mansoor, Manam, Real-time law cast infrared vein imaging system, 2013, Journal : Image Processing and Pattern Recognition.
Choi, Soo Joo; Gwak, Mi Sook; Ko, Justin Sang; Kim, Gaab Soo; Kim, Tae Hyeong; Ahn, Hyun; Kim, Jie Ae; Yang, Mikyung; Lee, Sang; Kim, Myung, Can peripheral venous pressure be an alternative to central venous pressure during right hepatectomy in living donors?, 2007, Journal : Liver Transplantation.
Beigel, Roy; Cercek, Bojan; Luo, Huai; Siegel, Robert J., Noninvasive Evaluation of Right Atrial Pressure, 2013, Journal : Journal of the American Society of Echocardiography.
Thomas, Michael; Shillingford, John, The Circulatory Response to a Standard Postural Change in Ischiemic Heart Disease, 1965, Journal : British Heart Journal.
Crimi, Alessandro; Makhinya, Maxim; Baumann, Ulrich; Thalhammer, Christoph; Szekely, Gabor; Goksel, Orcun, Automatic Measurement of Venous Pressure Using B-Mode Ultrasound, 2016, Journal : IEEE Transactions on Biomedical Engineering.

Spertus, John A.; Jones, Philip G., Development and Validation of a Short Version of the Kansas City Cardiomyopathy Questionnaire, 2015, Journal : Circulation: Cardiovascular Quality and Outcomes.
Song, In-Kyung; Park, Han-Seul; Lee, Ji-Hyun; Kim, Eun-Hee; Kim, Hee-Soo; Bahk, Jae-Hyon; Kim, Jin-Tae, Optimal level of the reference transducer for central venous pressure and pulmonary artery occlusion pressure monitoring in supine, prone, and sitting position, 2017, Journal : Journal of Clinical Monitoring and Computing.
Pellicori, Pierpaolo; Department of Cardiology, Castle Hill Hospital, Hull York Medical School (at University of Hull), Kingston upon Hull, UK; Kaur, Kuldeep; Department of Cardiology, Castle Hill Hospital, Hull York Medical School (at University of Hull), Kingston upon Hull, UK; Clark, Andrew L; Department of Cardiology, Castle Hill Hospital, Hull York Medical School (at University of Hull), Kingston upon Hull, UK, Fluid Management in Patients With Chronic Heart Failure, 2015, Journal : Cardiac Failure Review.
McGee, Steven R., Physical examination of venous pressure: A critical review, 1998, Journal : American Heart Journal.
Kircher, Barbara J.; Himelman, Ronald B.; Schiller, Nelson B., Noninvasive estimation of right atrial pressure from the inspiratory collapse of the inferior vena cava, 1990, Journal : The American Journal of Cardiology.
Jondeau, Guillaume; Detaint, Delphine; Arnoult, Florence; Phan, Gerald; Morgan, Catherine; Mercadier, Jean Jacques; Aumont, Marie Claude, Acute heart failure: How to evaluate left ventricular filling pressure in practice?, 2009, Journal : Archives of Cardiovascular Diseases.
Ilyas, Abid; Ishtiaq, Wasib; Assad, Salman; Ghazanfar, Haider; Mansoor, Salman; Haris, Muhammad; Qadeer, Aayesha; Akhtar, Aftab, Correlation of IVC Diameter and Collapsibility Index With Central Venous Pressure in the Assessment of Intravascular Volume in Critically Ill Patients, 2017, Journal : Cureus.
Givertz, Michael M; Slawsky, Mara T; Moraes, Denzil L; McIntyre, Kevin M; Colucci, Wilson S, Noninvasive determination of pulmonary artery wedge pressure in patients with chronic heart failure, 2001, Journal : The American Journal of Cardiology.
Economides, Evagoras; Stevenson, Lynne Warner, The jugular veins: Knowing enough to look, 1998, Journal : American Heart Journal.
Boehmer, John P; Wariar, Ramesh; Zhang, Yi; Thompson, Julie A; Herro, Gerard; Sweeney, Robert J; Hatlestad, John; Thakur, Pramodsingh; Averina, Viktoria; An, Qi, Rationale and Design of the Multisensor Chronic Evaluations in Ambulatory Heart Failure Patients (MultiSENSE) Study, 2015, Journal : The Journal of Innovations in Cardiac Rhythm Management.
Ward, Kevin R.; Tiba, Mohamad H.; Draucker, Gerard T.; Proffitt, Elizabeth K.; Barbee, Robert W.; Gunnerson, Kyle J.; Reynolds, Penny S.; Spiess, Bruce D., A Novel Noninvasive Impedance-Based Technique for Central Venous Pressure Measurement:, 2010, Journal : Shock.
Thalhammer, Christoph; Segerer, Stephan; Augustoni, Marlene; Jacomella, Vincenzo; Clemens, Robert K.; Wüthrich, Rudolf P.; Amann-Vesti, Beatrice R.; Husmann, Marc, Acute effects of haemodialysis on central venous and arterial pressure characteristics: Haemodynamic changes during haemodialysis, 2015, Journal : Nephrology.
Thalhammer, Christoph; Siegemund, Martin; Aschwanden, Markus; Gassmann, Mirjam; Baumann, Ulrich A.; Jaeger, Kurt A.; Imfeld, Stephan, Non-invasive central venous pressure measurement by compression ultrasound—A step into real life, 2009, Journal : Resuscitation.
Gauer, Otto H.; Sieker, Herbert O., The Continuous Recording of Central Venous Pressure Changes from an Arm Vein, 1956, Journal : Circulation Research.
Thalhammer, Christoph; Aschwanden, Markus; Odermatt, Angela; Baumann, Ulrich A.; Imfeld, Stephan; Bilecen, Deniz; Marsch, Stephan C.; Jaeger, Kurt A., Noninvasive Central Venous Pressure Measurement by Controlled Compression Sonography at the Forearm, 2007, Journal : Journal of the American College of Cardiology.
Early, Kirstin; Mankoff, Jennifer; Fienberg, Stephen E., Dynamic Question Ordering in Online Surveys, 2016, Journal : arXiv:1607.04209 [stat].

(56) References Cited

OTHER PUBLICATIONS

Baumann, Ulrich A.; Marquis, Claudia; Stoupis, Christoforos; Willenberg, Thorsten Andreas; Takala, Jukka; Jakob, Stephan M., Estimation of central venous pressure by ultrasound, 2005, Journal : Resuscitation.
Pellicori, Pierpaolo; Clark, Andrew L.; Kallvikbacka-Bennett, Anna; Zhang, Jufen; Urbinati, Alessia; Monzo, Luca; Dierckx, Riet; Anker, Stefan D.; Cleland, John G.F., Non-invasive measurement of right atrial pressure by near-infrared spectroscopy: preliminary experience. A report from the SICA-HF study: Near-infrared spectroscopy in heart failure, 2017, Journal : European Journal of Heart Failure.
Braunschweig, F, Continous haemodynamic monitoring during withdrawal of diuretics in patients with congestive heart failure, 2002, Journal : European Heart Journal.
Buescher, C. D.; Nachiappan, B.; Brumbaugh, J. M.; Hoo, K. A.; Janssen, H. F., Experimental Studies of the Effects of Abnormal Venous Valves on Fluid Flow, 2008, Journal : Biotechnology Progress.
Bodson, Laurent; Vieillard-Baron, Antoine, Respiratory variation in inferior vena cava diameter: surrogate of central venous pressure or parameter of fluid responsiveness? Let the physiology reply, 2012, Journal : Critical Care.
Shah, Sunil; Laiquzzaman, Mohammed; Bhojwani, Rajan; Mantry, Sanjay; Cunliffe, Ian, Assessment of the Biomechanical Properties of the Cornea with the Ocular Response Analyzer in Normal and Keratoconic Eyes, 2007, Journal : Investigative Opthalmology & Visual Science.
Gheorghiade, Mihai; Follath, Ferenc; Ponikowski, Piotr; Barsuk, Jeffrey H.; Blair, John E.A.; Cleland, John G.; Dickstein, Kenneth; Drazner, Mark H.; Fonarow, Gregg C.; Jaarsma, Tiny; Jondeau, Guillaume; Sendon, Jose Lopez; Mebazaa, Alexander; Metra, Marco; Nieminen, Markku; Pang, Peter S.; Seferovic, Petar; Stevenson, Lynne W.; van Veldhuisen, Dirk J.; Zannad, Faiez; Anker, Stefan D.; Rhodes, Andrew; McMurray, John J.V.; Filippatos, Gerasimos, Assessing and grading congestion in acute heart failure: a scientific statement from the Acute Heart Failure Committee of the Heart Failure Association of the European Society of Cardiology and endorsed by the European Society of Intensive Care Medicine, 2010, Journal : European Journal of Heart Failure.
Abay, T. Y.; Kyriacou, P. A., Accuracy of reflectance photoplethysmography on detecting cuff-induced vascular occlusions, 2015, Conference: IEEE.
Stamper, Robert L., A History of Intraocular Pressure and Its Measurement:, 2011, Journal : Optometry and Vision Science.
Glass, Dianne H.; Roberts, Cynthia J.; Litsky, Alan S.; Weber, Paul A., A Viscoelastic Biomechanical Model of the Cornea Describing the Effect of Viscosity and Elasticity on Hysteresis, 2008, Journal : Investigative Opthalmology & Visual Science.
Ward, Kevin R.; Tiba, M. Hakam; Barbee, R. Wayne; Ivatury, Rao R.; Arrowood, James A.; Spiess, Bruce D.; Hummel, Russell, A new noninvasive method to determine central venous pressure, 2006, Journal : Resuscitation.
Michael, Goh Kah Ong; Connie, Tee; Teoh, Andrew Beng Jin, A Contactless Biometric System Using Palm Print and Palm Vein Features, 2011, Journal : Advanced Biometric Technologies.
Kurita, Yuichi; Kempf, Roland; Iida, Yoshichika; Okude, Jumpei; Kaneko, Makoto; Mishima, Hiromu K; Tsukamoto, Hidetoshi; Sugimoto, Eiichiro; Katakura, Seiki; Kobayashi, Ken; Kiuchi, Yoshiaki, Contact-Based Stiffness Sensing of Human Eye, 2008, Journal : IEEE Transactions on Biomedical Engineering.
Wang, Lingyu; Leedham, Graham, Near- and Far-Infrared Imaging for Vein Pattern Biometrics, 2006, Conference: IEEE.
Brown, E; Greenfield, D M; Goei, J S; Plassaras, G, Filling and emptying of the low-pressure blood vessels of the human forearm., 1966, Journal : Journal of Applied Physiology.
Christ, F.; Gamble, J.; Baschnegger, H.; Gartside, I. B., Relationship Between Venous Pressure and tissue Volume During Venous Congestion Plethysmography in Man, 1997, Journal : The Journal of Physiology.

Ewing, D J; Campbell, I W; Murray, A; Neilson, J M; Clarke, B F, Immediate heart-rate response to standing: simple test for autonomic neuropathy in diabetes., 1978, Journal : BMJ.
Wen, Xuebing; Zhao, Jiangwei; Liang, Xuezhang, Research on Enhancing Human Finger Vein Pattern Characteristics, 2010, Conference: IEEE.
Raju, S.; Varney, E.; Flowers, W.; Cruse, G., Effect of External Positive and Negative Pressure on Venous Flow in an Experimental Model, 2016, Journal : European Journal of Vascular and Endovascular Surgery.
Sahin, Altan; Salman, M Alper; Salman, A Ebru; Aypar, Ulka, Effect of Body Temperature on Peripheral Venous Pressure Measurements and Its Agreement with Central Venous Pressure in Neurosurgical Patients, 2005, Journal : J Neurosurg Anesthesiol.
Fletcher, Richard Ribon; Raghavan, Varsha; Zha, Rujia; Haverkamp, Miriam; Hibberd, Patricia L., Development of mobile-based hand vein biometrics for global health patient identification, 2014, Conference: IEEE.
Coudray, Alice; Romand, Jacques-André; Treggiari, Miriam; Bendjelid, Karim, Fluid responsiveness in spontaneously breathing patients: A review of indexes used in intensive care:, 2005, Journal : Critical Care Medicine.
Convertino, Victor A.; Grudic, Greg; Mulligan, Jane; Moulton, Steve, Estimation of individual-specific progression to impending cardiovascular instability using arterial waveforms, 2013, Journal : Journal of Applied Physiology.
Sathish, N; Singh, NaveenG; Nagaraja, Ps; Sarala, Bm; Prabhushankar, Cg; Dhananjaya, Manasa; Manjunatha, N, Comparison between noninvasive measurement of central venous pressure using near infrared spectroscopy with an invasive central venous pressure monitoring in cardiac surgical Intensive Care Unit, 2016, Journal : Annals of Cardiac Anaesthesia.
Ryder, Henry W; Molle, William E; Ferris, Eugene B, The Influence of the Collapsibility of Veins on Venous Pressure, Including a New Procedure for Measuring Tissue Pressure, 1944, Journal : The Journal of clinical investigation.
Sochowski, Randall A.; Dubbin, James D.; Naqvi, Salim Z., Clinical and hemodynamic assessment of the hepatojugular reflux, 1990, Journal : The American Journal of Cardiology.
Chernbumroong, Saisakul; Cang, Shuang; Atkins, Anthony; Yu, Hongnian, Elderly activities recognition and classification for applications in assisted living, 2013, Journal : Expert Systems with Applications.
DeBernardo, Christina, Central Venous Pressure, Presentation: IvyLeagueNurse.com Nov. 11, 2014.
Costanzo, Maria R.; Stevenson, Lynne W.; Adamson, Philip B.; Desai, Akshay S.; Heywood, J. Thomas; Bourge, Robert C.; Bauman, Jordan; Abraham, William T., Interventions Linked to Decreased Heart Failure Hospitalizations During Ambulatory Pulmonary Artery Pressure Monitoring, 2016, Journal : JACC: Heart Failure.
Kumar, Dharmendra; Ahmed, SyedMoied; Ali, Shahna; Ray, Utpal; Varshney, Ankur; Doley, Kashmiri, Correlation between central venous pressure and peripheral venous pressure with passive leg raise in patients on mechanical ventilation, 2015, Journal : Indian Journal of Critical Care Medicine.
Karantonis, D.M.; Narayanan, M.R.; Mathie, M.; Lovell, N.H.; Celler, B.G., Implementation of a Real-Time Human Movement Classifier Using a Triaxial Accelerometer for Ambulatory Monitoring, 2006, Journal : IEEE Transactions on Information Technology in Biomedicine.
Chua Chiaco, J. M. S.; Parikh, N. I.; Fergusson, D. J., The jugular venous pressure revisited, 2013, Journal : Cleveland Clinic Journal of Medicine.
Devine, Patrick J.; Sullenberger, Lance E.; Bellin, Daniel A.; Atwood, J Edwin, Jugular Venous Pulse: Window into the Right Heart:, 2007, Journal : Southern Medical Journal.
Halliwill, John R.; Minson, Christopher T.; Joyner, Michael J., Measurement of limb venous compliance in humans: technical considerations and physiological findings, 1999, Journal : Journal of Applied Physiology.
Garg, Naveen; Garg, Nitish, Jugular Venous Pulse : An Appraisal, 2000, Journal : Journal, Indian Academy of Clinical Medicine.

(56) References Cited

OTHER PUBLICATIONS

Amelard, Robert; Hughson, Richard L.; Greaves, Danielle K.; Pfisterer, Kaylen J.; Leung, Jason; Clausi, David A.; Wong, Alexander, Non-contact hemodynamic imaging reveals the jugular venous pulse waveform, 2016, Journal : arXiv:1604.05213 [physics].
Wang, L.; Leedham, G.; Cho, S.-Y., Infrared imaging of hand vein patterns for biometric purposes, 2007, Journal : IET Computer Vision.
Wang, Fengtao; Behrooz, Ali; Morris, Michael; Adibi, Ali, High-contrast subcutaneous vein detection and localization using multispectral imaging, 2013, Journal : Journal of Biomedical Optics.
Shykoff, Barbara E; Hawari, Feras I; Izzo, Joseph L, Diameter, pressure and compliance relationships in dorsal hand veins, 2001, Journal : Vascular Medicine.
Shan Juan Xie; JuCheng Yang; Sook Yoon; Lu Yu; Dong Sun Park, Guided Gabor Filter for Finger Vein Pattern Extraction, 2012, Conference: IEEE.
Geerts, Bart; de Wilde, Rob; Aarts, Leon; Jansen, Jos, Pulse Contour Analysis to Assess Hemodynamic Response to Passive Leg Raising, 2011, Journal :Journal of Cardiothoracic and Vascular Anesthesia.
Kunze, Kai; Lukowicz, Paul; Junker, Holger; Tröster, Gerhard; Kunze, Kai; Lukowicz, Paul; Junker, Holger; Tröster, Gerhard, Where am I: Recognizing On-body Positions of Wearable Sensors, 2005, Book Section: Springer Berlin Heidelberg.
Wassertheurer, S; Kropf, J; Weber, T; van der Giet, M; Baulmann, J; Ammer, M; Hametner, B; Mayer, C C; Eber, B; Magometschnigg, D, A new oscillometric method for pulse wave analysis: comparison with a common tonometric method, 2010, Journal : Journal of Human Hypertension.
Yang, Jinfeng; Shi, Yihua, Finger-vein ROI localization and vein ridge enhancement, 2012, Journal : Pattern Recognition Letters.
Constant, Jules, Using Internal Jugular Pulsations as a Manometer for Right Atrial Pressure Measurements, 2000, Journal : Cardiology.
Trost, Stewart G; Zheng, Yonglei; Wong, Weng-Keen, Machine learning for activity recognition: hip versus wrist data, 2014, Journal : Physiological Measurement.
Peng, Rong-Chao; Zhou, Xiao-Lin; Lin, Wan-Hua; Zhang, Yuan-Ting, Extraction of Heart Rate Variability from Smartphone Photoplethysmograms, 2015, Journal : Computational and Mathematical Methods in Medicine.
Rizkallah, Jacques; Jack, Megan; Saeed, Mahwash; Shafer, Leigh Anne; Vo, Minh; Tam, James, Non-Invasive Bedside Assessment of Central Venous Pressure: Scanning into the Future, 2014, Journal : PLoS ONE.
Bouzida, Nabila; Bendada, Abdel Hakim; Maldague, Xavier P., Near-infrared image formation and processing for the extraction of hand veins, 2010, Journal : Journal of Modern Optics.
Najafi, B.; Aminian, K.; Paraschiv-Ionescu, A.; Loew, F.; Bula, C.J.; Robert, P., Ambulatory system for human motion analysis using a kinematic sensor: monitoring of daily physical activity in the elderly, 2003, Journal : IEEE Transactions on Biomedical Engineering.
Najafi, B.; Aminian, K.; Loew, F.; Blanc, Y.; Robert, P.A., Measurement of stand-sit and sit-stand transitions using a miniature gyroscope and its application in fall risk evaluation in the elderly, 2002, Journal : IEEE Transactions on Biomedical Engineering.
Monnet, Xavier; Teboul, Jean-Louis, Passive leg raising: five rules, not a drop of fluid!, 2015, Journal : Critical Care.
Monnet, Xavier; Lamia, Bouchra; Teboul, Jean-Louis, Pulse oximeter as a sensor of fluid responsiveness: do we have our finger on the best solution?, 2005, Journal : Critical Care.
Piccini, Jonathan P.; Hranitzky, Patrick, Diagnostic monitoring strategies in heart failure management, 2007, Journal : American Heart Journal.
Martinez, Ricky; Fierro, Cesar A.; Shireman, Paula K.; Han, Hai-Chao, Mechanical Buckling of Veins Under Internal Pressure, 2010, Journal : Annals of Biomedical Engineering.
Herndon, Leon W., Measuring intraocular pressure-adjustments for corneal thickness and new technologies:, 2006, Journal : Current Opinion in Ophthalmology.
Albert, N. M., Fluid Management Strategies in Heart Failure, 2012, Journal : Critical Care Nurse.
Marik, P.E.; Lemson, J., Fluid responsiveness: an evolution of our understanding, 2014, Journal : British Journal of Anaesthesia.
Levick, J. R., An introduction to cardiovascular physiology, 1991, Book: Butterworths.
Shahzad, A.; Walter, N.; Malik, Aamir Saeed; Saad, N. M.; Meriaudeau, F., Multispectral venous images analysis for optimum illumination selection, 2013, Conference: IEEE.
Paquit, Vincent; Price, Jeffery R.; Mériaudeau, Fabrice; Tobin, Jr., Kenneth W.; Ferrell, Thomas L., Combining near-infrared illuminants to optimize venous imaging, 2007, Conference: Proc. SPIE 6509, Medical Imaging 2007: Visualization and Image-Guided Procedures, 65090H (Mar. 21, 2007).
Spodick, David H.; Quarry-Pigott, Veronica M., Effects of Posture on Exercise Performance: Measurement by Systolic Time Intervals, 1973, Journal: Circulation.
Miyamoto, Y.; Higuchi, J.; Abe, Y.; Hiura, T.; Nakazono, Y.; Mikami, T., Dynamics of cardiac output and systolic time intervals in supine and upright exercise, 1983, Journal : Journal of Applied Physiology.
Wiens, Andrew D, Detecting Aortic Valve Opening and Closing from Distal Body Vibrations, 2016, Journal : rXiv preprint arXiv: https://arxiv.org/abs/1609.08208. Sep. 2016.
Hickey, Michelle; Phillips, Justin P.; Kyriacou, Panayiotis A., Investigation of peripheral photoplethysmographic morphology changes induced during a hand-elevation study, 2016, Journal : Journal of Clinical Monitoring and Computing.
Sola, Josep; Chetelat, Olivier, Combination of multiple light paths in pulse oximetry: the finger ring example, 2007, Conference: IEEE.
Lance, V Q; Spodick, D H, Heart rate—left ventricular ejection time relations. Variations during postural change and cardiovascular challenges., 1976, Journal : Heart.
Lewin, Jennifer; Ledwidge, Mark; O'Loughlin, Christina; McNally, Clare; McDonald, Ken, Clinical deterioration in established heart failure: What is the value of BNP and weight gain in aiding diagnosis?, 2005, Journal : European Journal of Heart Failure.
Winsor, Travis; Burch, George E, Use of the Phlebomanometer: Normal venous pressure values and a study of certain clinical aspects of venous hypertension in man, 1946, Journal : American Heart Journal.
Jakovels, Dainis; Rubins, Uldis; Spigulis, Janis, RGB imaging system for mapping and monitoring of hemoglobin distribution in skin, 2011, Conference: Image Spectrometry XVI, Proc. of SPIE vol. 8158, 2011.
Gavish, Benjamin; Gavish, Leah, Blood pressure variation in response to changing arm cuff height cannot be explained solely by the hydrostatic effect, 2011, Journal : Journal of Hypertension.
Han, Fei; Reily, Brian; Hoff, William; Zhang, Hao, Space-time representation of people based on 3D skeletal data: A review, 2017, Journal : Computer Vision and Image Understanding.
Stevenson, Lynne Warner; Perloff, Joseph K., The Limited Reliability of Physical Signs for Estimating Hemodynamics in Chronic Heart Failure, 1989, Journal : JAMA.
Cook, Deborah J.; Simel, David L., Does This Patient Have Abnormal Central Venous Pressure?, 1996, Journal : JAMA.
Amoroso, P.; Greenwood, R. N., Posture and central venous pressure measurement in circulatory volume depletion, 1989, Journal : Lancet.
Applefeld, Mark M, The Jugular Venous Pressure and Pulse Contour-annotated.pdf, 1990, Journal : Clinical methods: The history, physical, and laboratory examinations.
Radcliffe, Nathan M., Hysteresis_ A Powerful Tool for Glaucoma Care, 2014, Journal : Review of Ophthalmology.

* cited by examiner

FIG. 17A
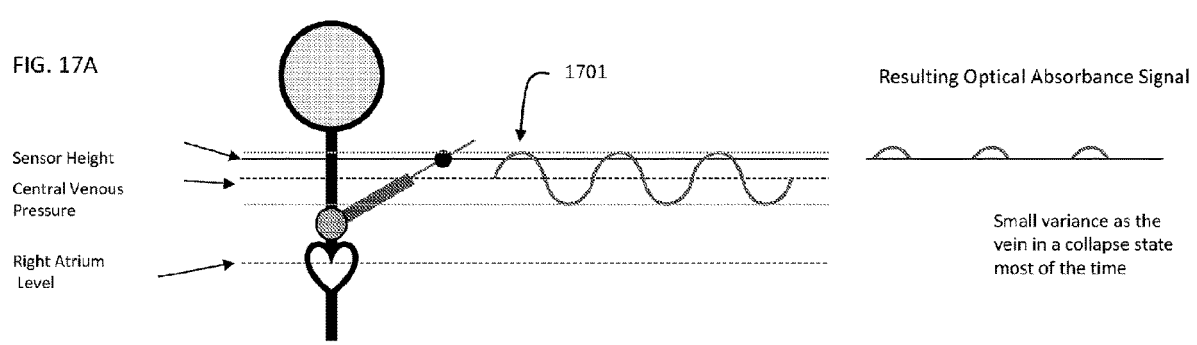
FIG. 17B
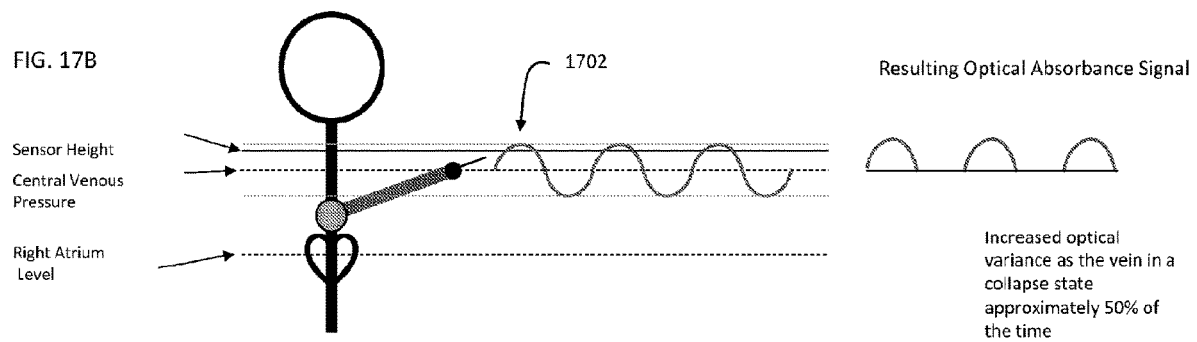
FIG. 17

FIG. 18A
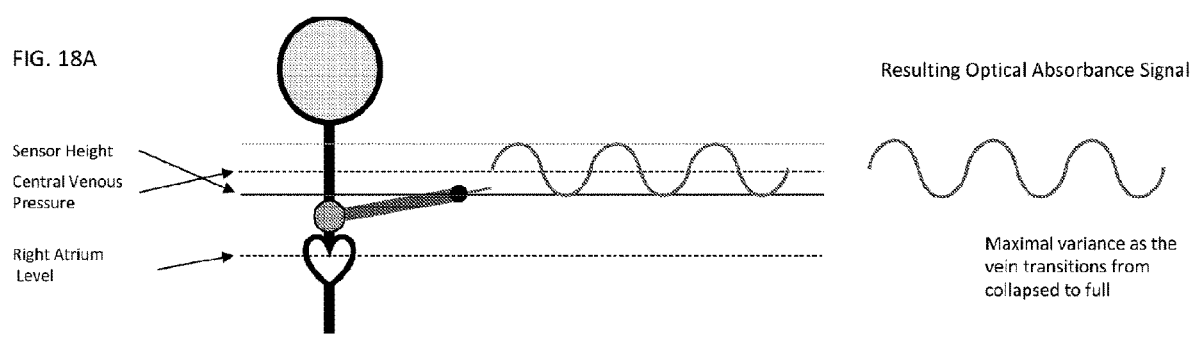
Resulting Optical Absorbance Signal
Maximal variance as the vein transitions from collapsed to full
FIG. 18B
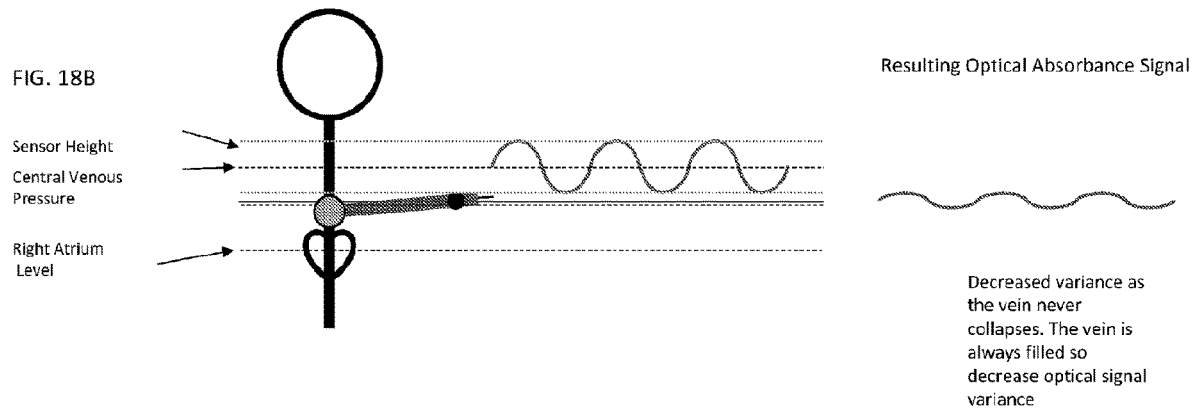
Resulting Optical Absorbance Signal
Decreased variance as the vein never collapses. The vein is always filled so decrease optical signal variance
FIG. 18

FIG. 20A
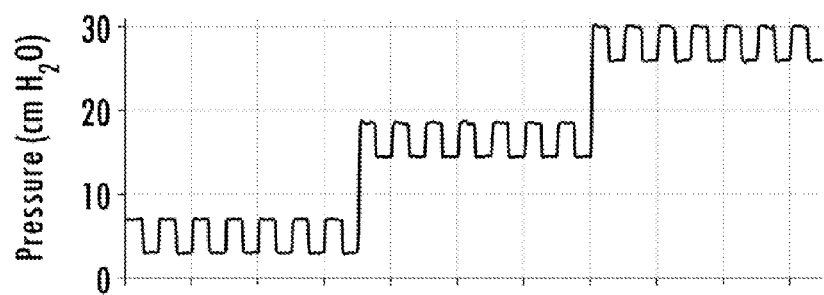
FIG. 20B
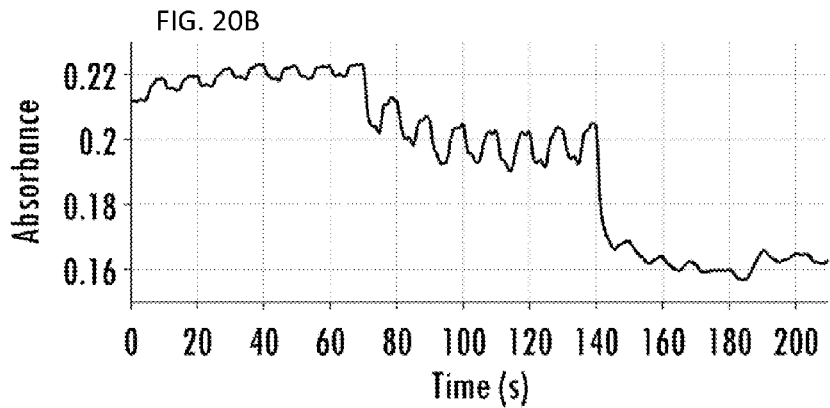
FIG. 20

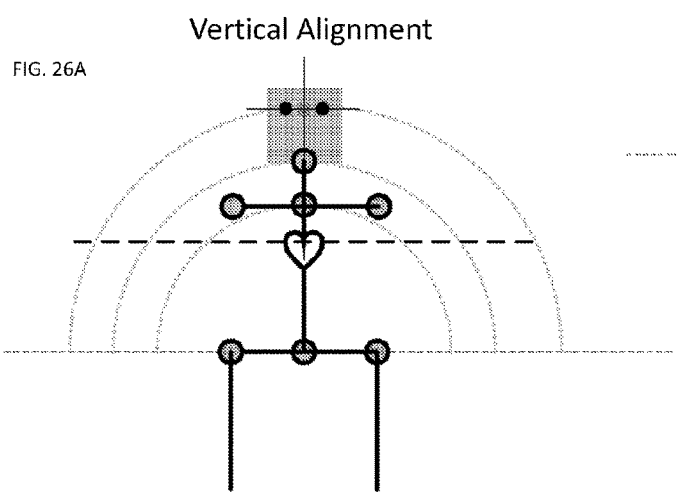
FIG. 26A
Vertical Alignment
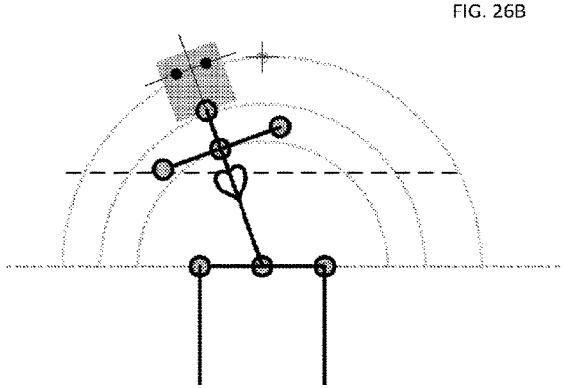
FIG. 26B
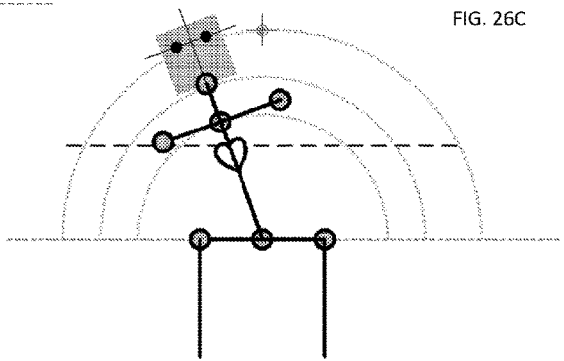
FIG. 26C
FIG. 26

FIG. 28A
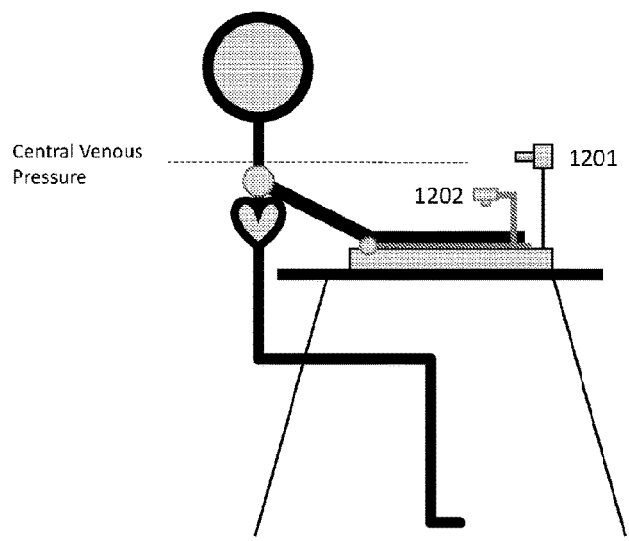
FIG. 28B
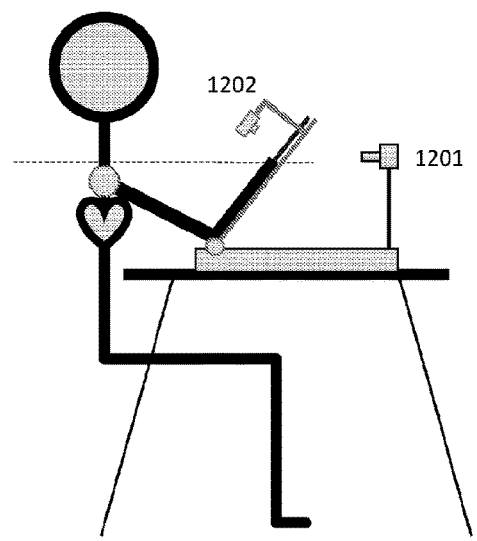
FIG. 28

FIG. 30A
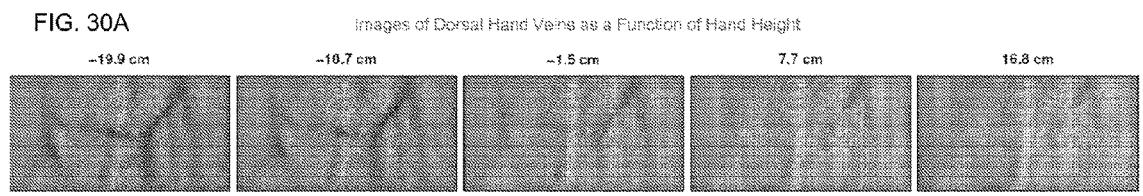
FIG. 30B
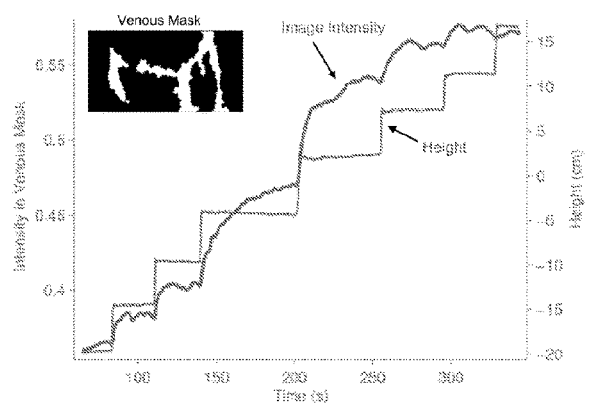
FIG. 30C
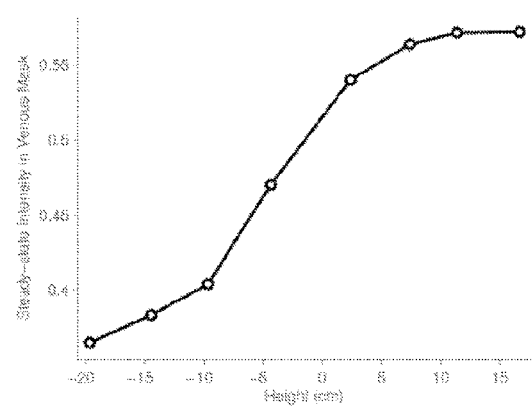
FIG. 30

FIG. 34A
Images of Dorsal Hand Veins as a Function of Dynamic Air Flow
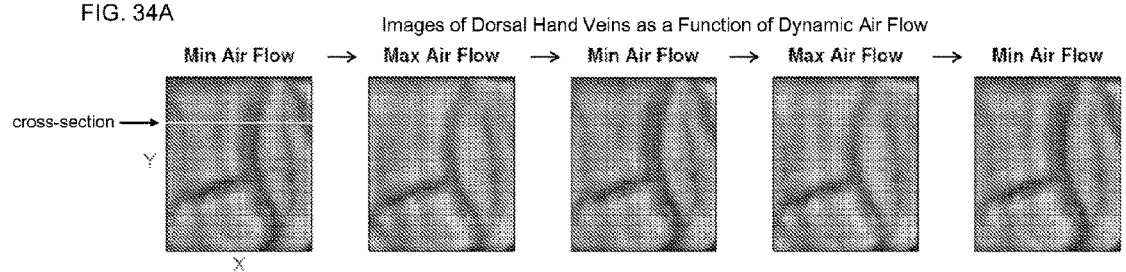
FIG. 34B
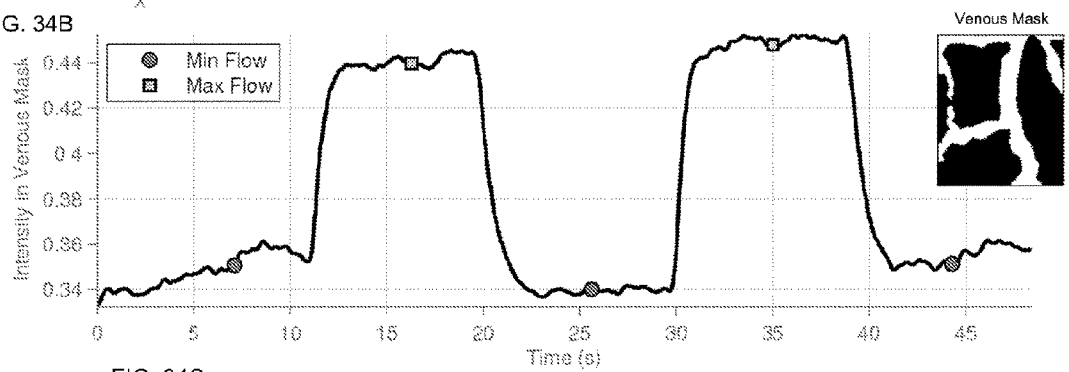
FIG. 34C
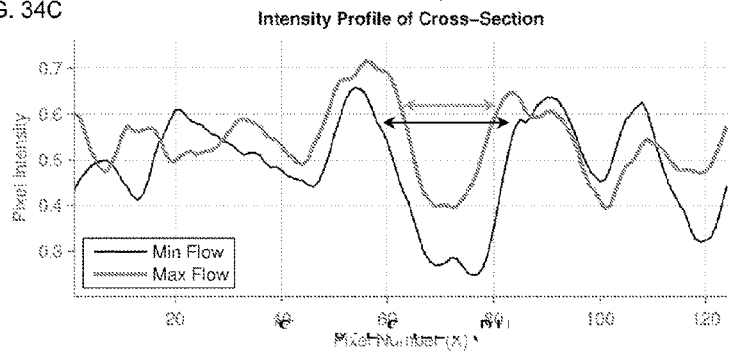
FIG. 34

FIG. 37A
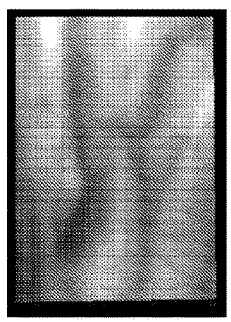
FIG. 37B
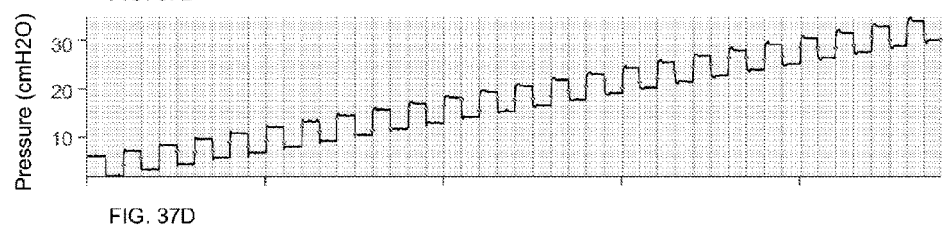
FIG. 37D
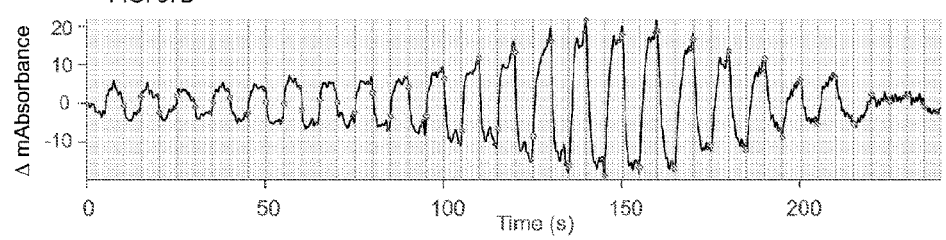
FIG. 37C
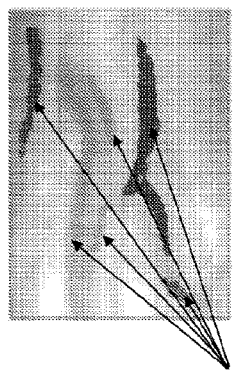
3701
FIG. 37E  Venous Clusters
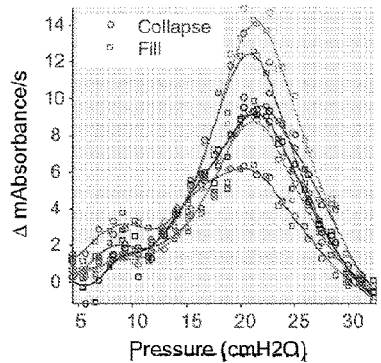
FIG. 37F  All Venous Pixels
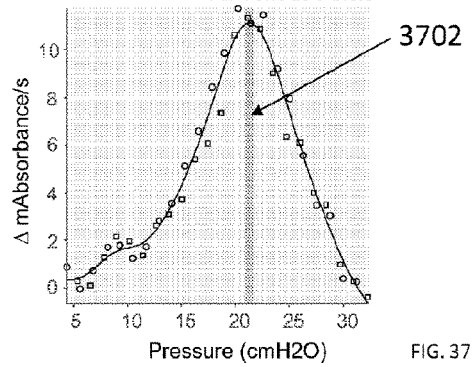
3702
FIG. 37

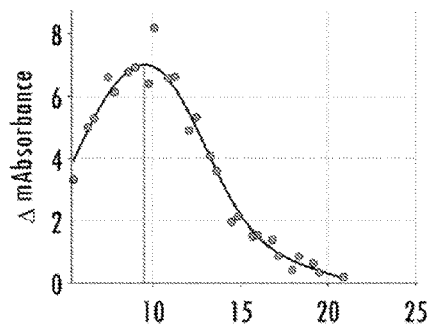
FIG. 38A
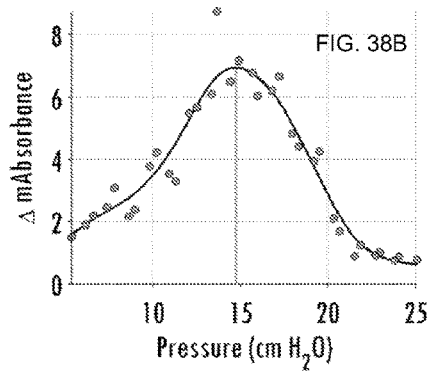
FIG. 38B
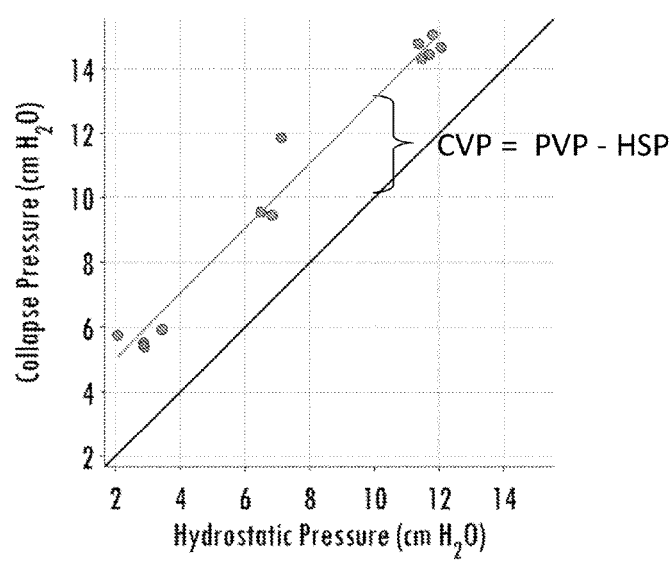
FIG. 38C
FIG. 38

METHODS AND APPARATUSES FOR CENTRAL VENOUS PRESSURE MEASUREMENT STATUS

CROSS-REFERENCE TO RELATED APPLICATIONS

This application is a national stage application under 35 U.S.C. 371 of PCT application PCT/US2017/062366, filed 17 Nov. 2017, which claims priority to U.S. provisional application 62/423,768, filed 17 Nov. 2016. Each of the foregoing is incorporated by reference herein.

TECHNICAL FIELD

The present invention relates to methods for determining central venous pressure, and apparatuses configured to determine central venous pressure.

BACKGROUND ART

The central venous pressure (CVP) refers to the mean vena cava or right atrial pressure, which is equivalent to right ventricular end-diastolic pressure in the absence of tricuspid stenosis. The higher the CVP, the greater the passive diastolic filling of the right ventricle. Per Starling's cardiac function curves in normal hearts, greater filling of the right ventricle leads to a larger right ventricular stroke volume on the subsequent beat. CVP is expressed in millimeters of mercury (mm Hg) or centimeters of water (cm H2O) above atmospheric pressure (1.36 cm H2O=1.0 mm Hg). In most patients, the mean right atrial pressure measured by the CVP closely resembles the mean left atrial pressure (LAP). At the end of diastole, left atrial pressure is assumed to equal left ventricular end diastolic pressure (LVEDP), which in turn is assumed to reflect left ventricular end diastolic volume (LVEDV). Thus, CVP reflects left ventricular preload, a critical parameter in optimizing cardiac function. However, in patients with obstruction, or valvular problems or pulmonary disease the right and left ventricles may function independently. In these less common cases, left ventricular preload should be estimated by measuring the pulmonary capillary 'wedge' pressure, using a pulmonary artery catheter (PAC), as this is a better guide to the venous return to the left side of the heart than CVP.

Central venous pressure (CVP) measurement is essential for monitoring hemodynamics in critically ill patients, individuals with heart failure, and patients undergoing surgery to estimate cardiac preload and circulating blood volume. The current standard technique for measurement of CVP is invasive, requiring insertion of a catheter into a subclavian or internal jugular vein, with potential complications. As CVP is the pressure at the right atrium, the system must be "zero-ed" relative to the location of the right atrium or the phlebostatic axis. This reference point is located at the intersection of the fourth intercostal space and mid-axillary line, allowing the measurement to be as close to the right atrium as possible.

CVP can be estimated by physical examination of the jugular veins of the neck. The external jugular vein runs over the sternomastoid muscle and the internal jugular vein runs deep to it. With the subject in a semi-supine position, the lower part of the external jugular vein is normally distended while the upper part is collapsed. Thus, jugular venous pressure (JVP) provides an indirect measure of central venous pressure. The internal jugular vein connects to the right atrium without any intervening valves, acting as a column for the blood in the right atrium. Unfortunately, JVP measurements are difficult and measurement prone due to variance in patient position and clinician measurement techniques. A 1996 systematic review by Cook et al concluded that agreement between doctors on the jugular venous pressure can be poor. Cook, Deborah J., and David L. Simel. "Does this patient have abnormal central venous pressure?." Jama 275.8 (1996): 630-634. When determining CVP in a heart failure patient by JVP examination, there is the mistaken belief that jugular pulsations are easier to see if the patient is in fluid overload. However, because jugular pulsations depend on right atrial and ventricular contraction, if the patient is in heart failure with a low ejection fraction, the pulsations may be difficult to perceive.

A simple, accurate, noninvasive, and self-administered determination of CVP would represent a valuable tool in the assessment of cardiac function and overall hemodynamic status to include volume status, fluid overload, and left ventricular end diastolic pressure (LVEDP). Such a self-administered test would have significant value in the ambulatory monitoring of the patent with congestive heart failure.

Heart failure occurs due to inadequate cardiac output. Management goals are thus focused on the optimization of stroke volume for the patient with limited cardiac function. Stroke volume is critically dependent on the volume of blood in the left ventricle at the end of diastole, the end diastolic volume. FIG. 1 is a graphical representation of heart performance of a patient with heart failure. The overall performance of the heart in a patient with heart failure is defined by decreased stroke volume when the end diastolic filling pressure exceeds an optimal level. Optimal performance of the heart occurs over a limited range of end diastolic pressures and is labeled "target volume" in the figure and is represented using Frank-Starling curve. Thus, fluid management in these patients is critical; too little fluid leads to decreases stroke volume while fluid overload also leads to decreased stroke volume.

Heart failure is a significant medical problem with an estimated US cost of approximately $30 billion annually with 80% of that expenditure being attributable to hospital admissions. The ability to reduce hospital admissions by improved ambulatory management has been a long-standing clinical objective. The primary cause of heart failure-related hospitalizations is fluid overload. Historical monitoring methods for fluid overload, such as shortness of breath, swelling, fatigue, and weight gain, are not sensitive enough to reflect early pathophysiologic changes that increase the risk of decompensation and subsequent admission to the hospital. Lewin J, Ledwidge M, O'Loughlin C, McNally C, McDonald K. Clinical deterioration in established heart failure: what is the value of BNP and weight gain in aiding diagnosis? Eur J Heart Fail. 2005; 7(6):953-957. Stevenson L, Perloff J K. The limited reliability of physical signs for estimating hemodynamics in chronic heart failure. JAMA. 1989; 261(6):884-888. FIG. 2 shows a typical clinical course of a heart failure patient with increasing fluid overload resulting in hospitalization. Examination of the figure shows that clinically observable signs occur late in the overall decompensation sequence. Thus, the use of clinical symptoms for the management of heart failure patients is problematic.

The difficulty of determining early hemodynamic congestion is demonstrated by the recently completed Better Effectiveness After Transition-Heart Failure (BEAT-HF) study. The study involving more than 1400 patients who were extensively monitored with existing noninvasive technology. The study investigated aggressive management of heart failure patients using a protocol that included pre-discharge heart-failure education, regularly scheduled telephone coaching, and telemonitoring. Telemonitoring included a BLUETOOTH enabled weight scale and blood-pressure/heart-rate monitor integrated with a text device that sent the information to a centralized call center for review (BLUETOOTH is a wireless technology standard used for exchanging data between fixed and mobile devices over short distances using short-wavelength UHF radio waves in the industrial, scientific and medical radio bands, from 2.400 to 2.485 GHz). If predetermined thresholds were exceeded, the patient was called and medication changed as determined by the clinical staff. Also, if significant symptoms were reported, the patient's heart-failure physician was notified and the patient was sent to the emergency department, if necessary. The conclusion from this extensive clinical study was that the intervention had no significant effect on hospital readmission rates.

Decreases in hospital admission rates have been demonstrated by using an invasive-implanted pulmonary artery pressure monitoring system. The CARDIOMEMS HF System measures and monitors the pulmonary artery (PA) pressure and heart rate in heart failure patients. The System consists of an implantable PA sensor, delivery system, and Patient Electronics System. The implantable sensor is permanently placed in the pulmonary artery, the blood vessel that moves blood from the heart to the lungs. The sensor is implanted during a right heart catheterization procedure. The Patient Electronics System includes the electronics unit and antenna. The Patient Electronics System wirelessly reads the PA pressure measurements from the sensor and then transmits the information to the doctor. After analyzing the information, the doctor may make medication changes to help treat the patient's heart failure. In a clinical study in which 550 participants had the device implanted, there was a clinically and statistically significant reduction in heart failure-related hospitalizations for the participants whose doctors had access to PA pressure data. The system costs approximately $2,000 to implant and has a list price of $18,000.

An accurate, self-administered, and noninvasive measurement of CVP would be a significant medical advancement as it would provide information of comparable value to the expensive, invasive CARDIOMEMS system. Specifically, CVP is a measure of right atrial pressure and closely resembles the mean left atrial pressure (LAP). At end diastole left atrial pressure is assumed to equal left ventricular end diastolic pressure (LVEDP), which in turn is assumed to reflect left ventricular end diastolic volume (LVEDV). Thus, CVP is directly related to left ventricular preload, a key parameter in optimizing cardiac output in the heart failure patient.

SUMMARY OF INVENTION

Embodiments of the present invention address the limitations of current central venous pressure monitoring by providing a noninvasive, non-implanted, and self-administered test for the determination of central venous pressure. The system uses alterations in transmural pressure, optical measurements of venous volume, and anatomical measurements to determine central venous pressure. The system can provide an absolute measurement of central pressure or can be used to monitor relative changes in central venous pressure over time. Changes in transmural pressure are used to create detectable changes in peripheral venous vascular volume for central venous pressure measurement. Transmural pressure changes can be induced by intravascular or extravascular pressure changes. The system noninvasively measures changes in venous volume in the presence of prescribed transmural pressure changes. The relationship between the transmural pressure change and the change in vascular venous volume is used with anatomical measurements to determine the central venous pressure of the patient. Changes in central venous pressure are correlated with cardiovascular function and can be used for the effective management of heart failure patients.

The measurement process uses optical detection methods that are sensitive to venous volume changes. These optical changes can be used to determine the central venous pressure in the presence of defined transmural pressure changes. The optical measurement system interacts with the venous system in a noncontact manner or in a defined contact manner. The measurement process addresses nuances of the measurement including delays in venous volume response, autonomic function, positional sensitivities, and anatomical differences between patients. The measured central venous pressure provides a cardiovascular assessment to facilitate the management of heart failure patient in a proactive manner for the avoidance of fluid overload and possible admission to the hospital.

BRIEF DESCRIPTION OF DRAWINGS

FIG. 17 is an illustration of breathing-induced time varying transmural pressure changes.

FIG. 18 is a second illustration of breathing-induced time varying transmural pressure changes.

FIG. 20 is an example of vein imaging during extravascular variations in transmural pressure.

FIG. 26 is a second example subject repositioning using head position.

FIG. 28 is an illustration of an anatomical measurement and controlled arm movement system.

FIG. 30 is an example of vein imaging with a controlled arm raise.

FIG. 34 is an example of vein volume changes induced by air pressure.

FIG. 37 demonstrates central venous pressure determination using static air pressure to change transmural pressure.

FIG. 38 demonstrates the sensitivity of the central venous pressure using static air pressure.

DESCRIPTION OF EMBODIMENTS AND INDUSTRIAL APPLICABILITY

Definitions

Figure 1:
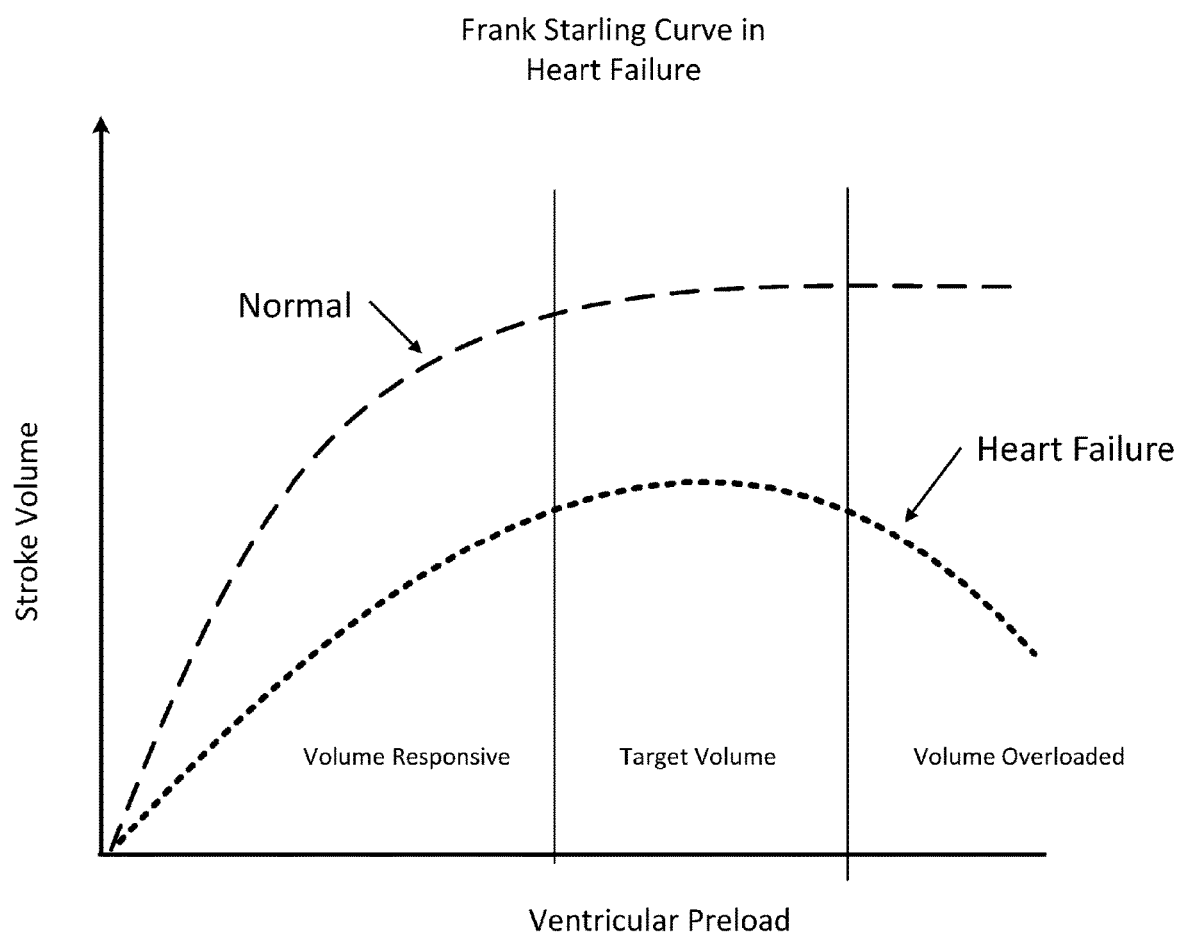
FIG. 1 is a schematic representation of the Frank Starling Curve.
Figure 2:
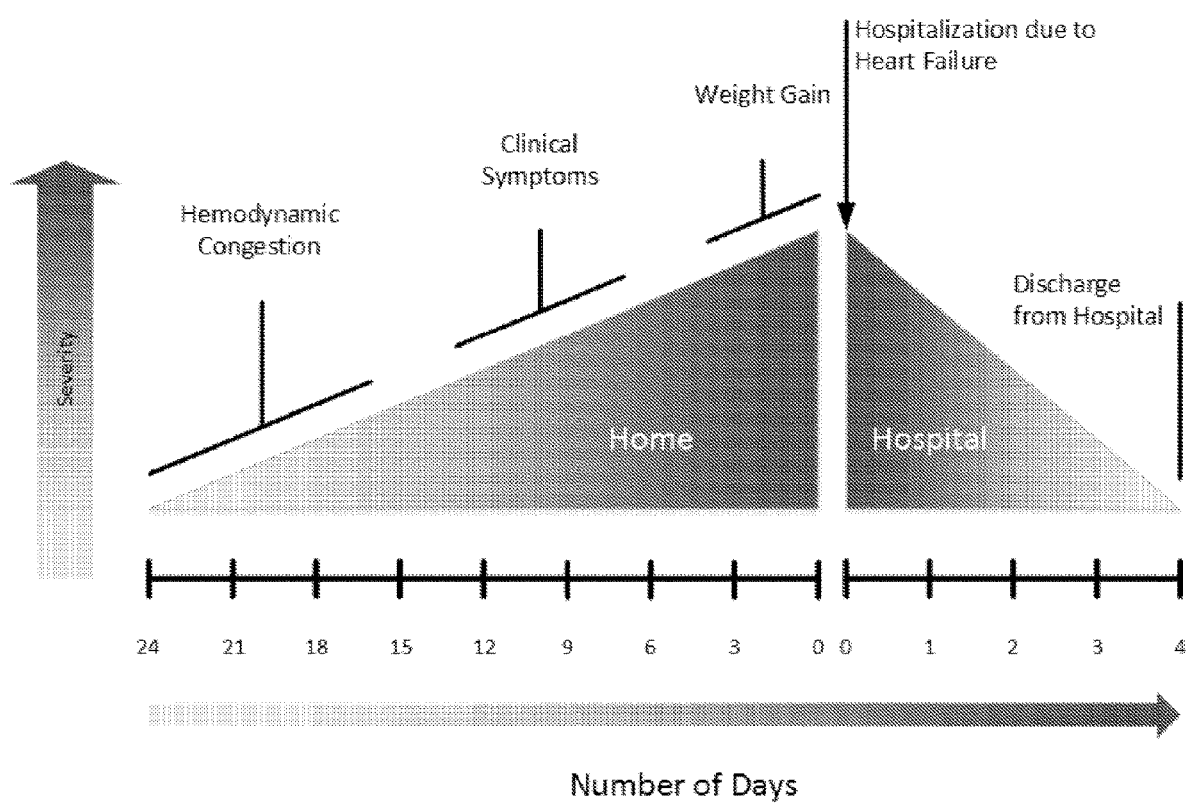
FIG. 2 is a schematic representation of hemodynamic congestion over time.

Transmural pressure is a general term that describes the pressure across the wall of a vessel (transmural literally means "across the wall"), and is defined by the following equation:

$$P_{TM} = P_{Inside} - P_{Outside}$$

A flexible container expands if there is a positive transmural pressure (pressure greater inside than outside the object) and contracts with a negative transmural pressure. A positive transmural pressure is sometimes referred to as a "distending" pressure. A transmural pressure change refers to any mechanism that changes the relationship between inside pressure and outside pressure. Methods for changing inside or intravascular pressure include but are not limited to positional changes, hydrostatic pressure changes, stroke volume changes, vascular volume changes, cardiac contractility changes, and exercise. Methods for changing outside or extravascular pressure include but are not limited to changes in intrathoracic pressure, positional changes, compression of the vasculature by water, air or other means, use of vacuum methodologies, resistance breathing, mechanical breathing, abdominal compression, Valsalva, Mueller maneuvers, and muscle contraction.

Resistance breathing is a general term that applies to any method that increases, decreases, or changes intrathoracic pressure as compared with normal breathing. Resistance breathing tests can include inhalation resistance breathing, and exhalation resistance breathing, independently or in combination. The use of exhalation resistance breathing will create an increase in intrathoracic pressure while the use of inhalation resistance breathing creates decreased intrathoracic pressures. Resistance breathing can be conducted using various protocols, such as paced breathing and event-defined breathing. Paced breathing defines target times for inhalation and exhalation such that the breathing rate is constant. Event-defined breathing is a type of resistance breathing where the subject exhales or inhales against resistance for a single breath followed by rest or recovery period. The term resistance breathing also covers the process of creating a change in intrathoracic pressure where little or no air movement occurs. The creation of an occlusion pressure either increased or decreased is encompassed as part of the broad definition of resistance breathing.

Hydrostatic positional change is a general term that applies to any process that changes the hydrostatic pressure in a vessel due to positional changes or other means.

Heart Failure Etiology and CVP Measurement

Due to the etiology of heart failure, changes in cardiovascular function are associated with changes in overall fluid status, and are reflected in central venous pressure or hemodynamic congestion. Determination of hemodynamic congestion is the critical metric of cardiovascular evaluation in the patient with heart failure, however current methods of determination are not applicable in the home setting. Invasive measurements provide accurate estimation of central venous pressure, but they are impractical for ambulatory patients. Implanted technologies have applicability, but are expensive. Ultrasound or echocardiography methods can estimate elevated central pressure, but are time consuming and require trained operators.

Vein Hemodynamics

The invention recognizes that peripheral venous pressure (PVP) reflects an 'upstream' venous variable which is coupled to the CVP by a continuous column of blood, analogous to the fluid continuity that exists between a pulmonary artery occlusion catheter and the left atrium. Synder C L, Saltzman D, Happe J, Eggen M A, Ferrell K L, Leonard A S. Peripheral venous monitoring with acute blood Volume alteration: cuff-occluded rate of rise of peripheral venous pressure. Crit Care Med 1990; 18: 1142-5.3.

Figure 3:
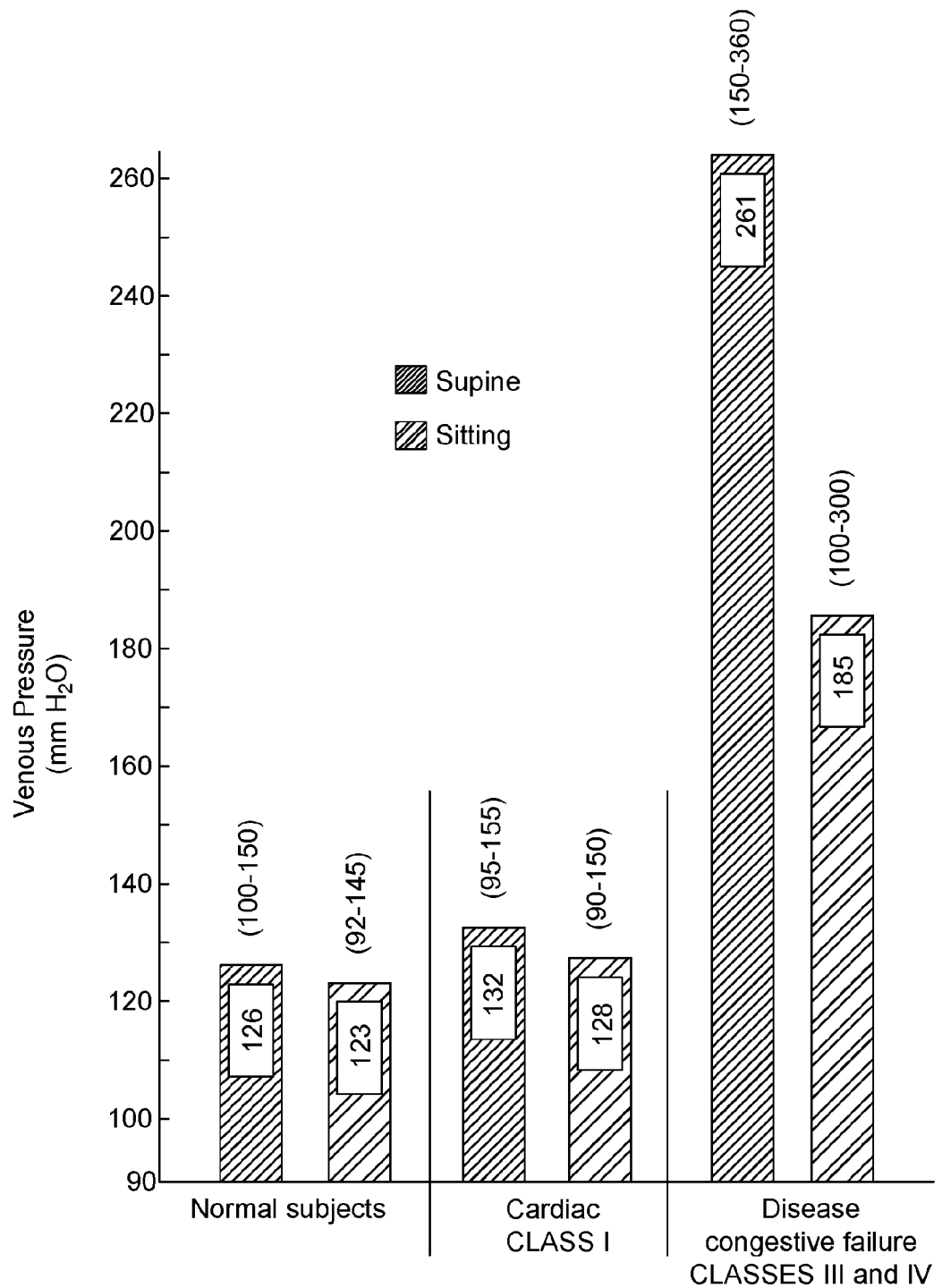
FIG. 3 is a plot of peripheral venous pressure in heart disease.

The relationship between peripheral venous pressure and the differential diagnosis and clinical management of heart disease was studied in 1945 by Winsor et al. The authors demonstrated increased venous pressures in the median basilica vein in patients with heart failure. FIG. 3 is reproduced from the publication and shows the significant increase in peripheral venous pressure in subjects with Class III and IV heart disease. The measurements presented were made by a phlebomanometer, an invasive venous catheter with a pressure measurement system. The invention also recognizes that CVP significantly drops when patients with intravascular volume depletion or heart failure sit up, also shown in FIG. 3. Winsor, Travis, and George E. Burch. "Use of the phlebomanometer: Normal venous pressure values and a study of certain clinical aspects of venous hypertension in man." American heart journal 31.4 (1946): 387-406.

Venous Distention Curve

Figure 4:
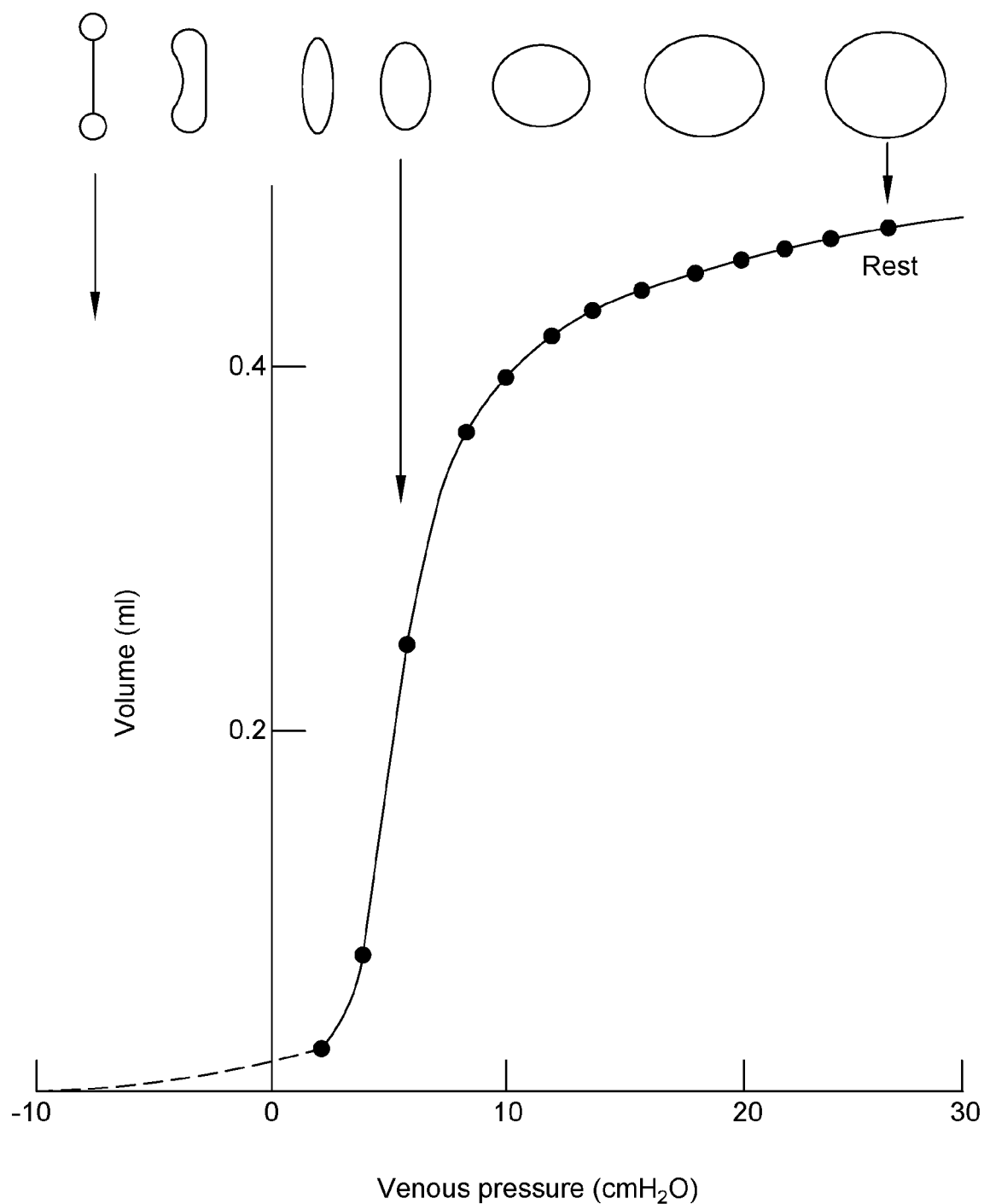
FIG. 4 is a schematic illustration of the distensibility of a vein.

Peripheral venules and veins are thin-walled, voluminous vessels, and contain roughly two-thirds of the circulating blood. The venous system acts as a variable reservoir of blood for the thoracic compartment and influences cardiac filling pressure. The effect of pressure on venous volume is particularly steep between zero and 10 mmHg because the thin-walled vein deforms easily, as shown in FIG. 4. Below zero transmural pressure, the vein collapses into a dumbbell shape and any flow is confined to the marginal channels. At a transmural pressure of 1 mmHg, the vein is almost collapsed and has a narrow elliptical profile. As pressure rises towards 10 mmHg, the elliptical profile becomes progressively rounder, enabling the vein to accommodate large volume changes with just a few mmHg of pressure change. Above 10-15 mmHg the profile is fully circular and since the stretched collagen in the wall is relatively inextensible the volume is less sensitive to pressures over 15 mmHg. The maximum distensibility (change in volume/ change in pressure), occurs at approximately 4 mmHg. For the venous system distensibility is estimated to be approximately 100 ml/mmHg, over 50 times greater than the arterial system.

Within the intact vascular system, blood enters from the capillaries into the venules at a pressure of approximately 12-20 mmHg. By the time it reaches larger, named veins such as the brachial vein, pressure has fallen to approximately 8-10 mmHg. The subsequent venous resistance is very small (except in collapsed vessels) thus the 8-10 mmHg pressure head is sufficient to drive the cardiac output from the periphery into the central veins and right ventricle, where the diastolic pressure is 0-6 mmHg.

Relationship between Venous Collapse and CVP

Figure 5:
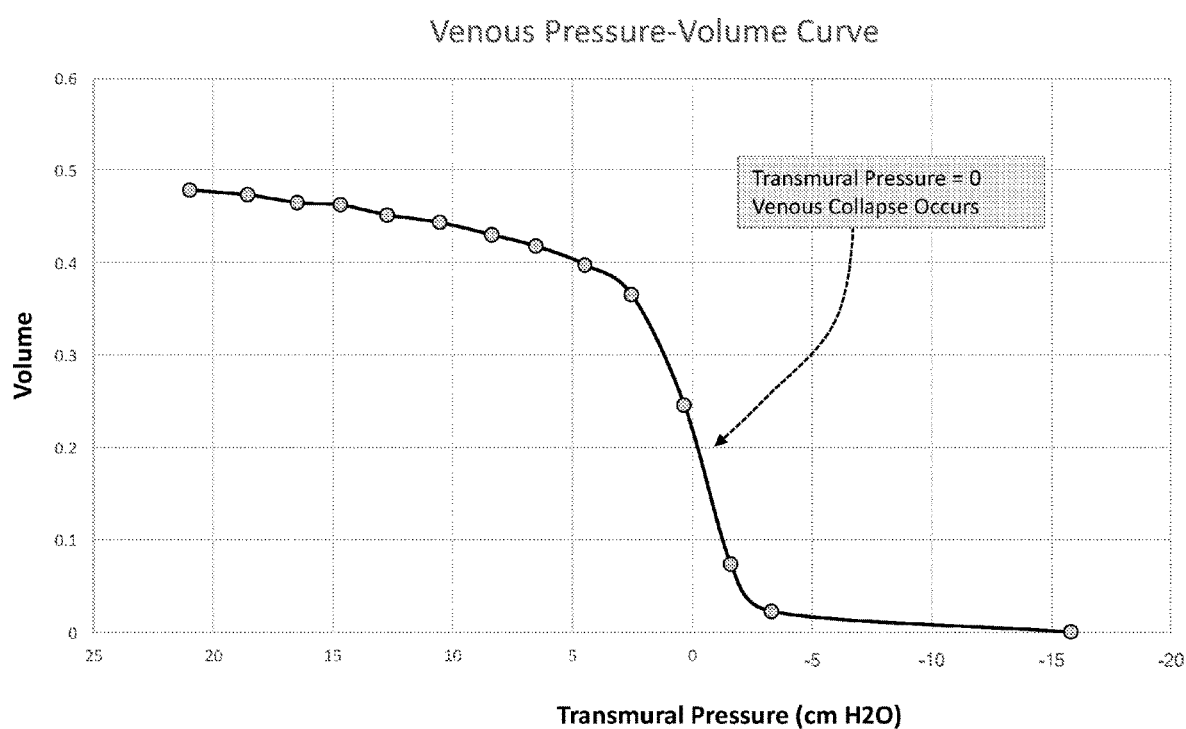
FIG. 5 is a plot for volume change versus venous pressure.

For clarity, the distensibility curve of FIG. 4 has been replotted in FIG. 5 and pressure is now expressed as the transmural pressure, with positive transmural pressure on the left side of the abscissa. Full venous collapse occurs when the transmural pressure is zero or less than zero. Thus, FIG. 5 shows the transmural pressure change due to arm movement on the x-axis and decreasing volume is on the y-axis.

Figure 6:
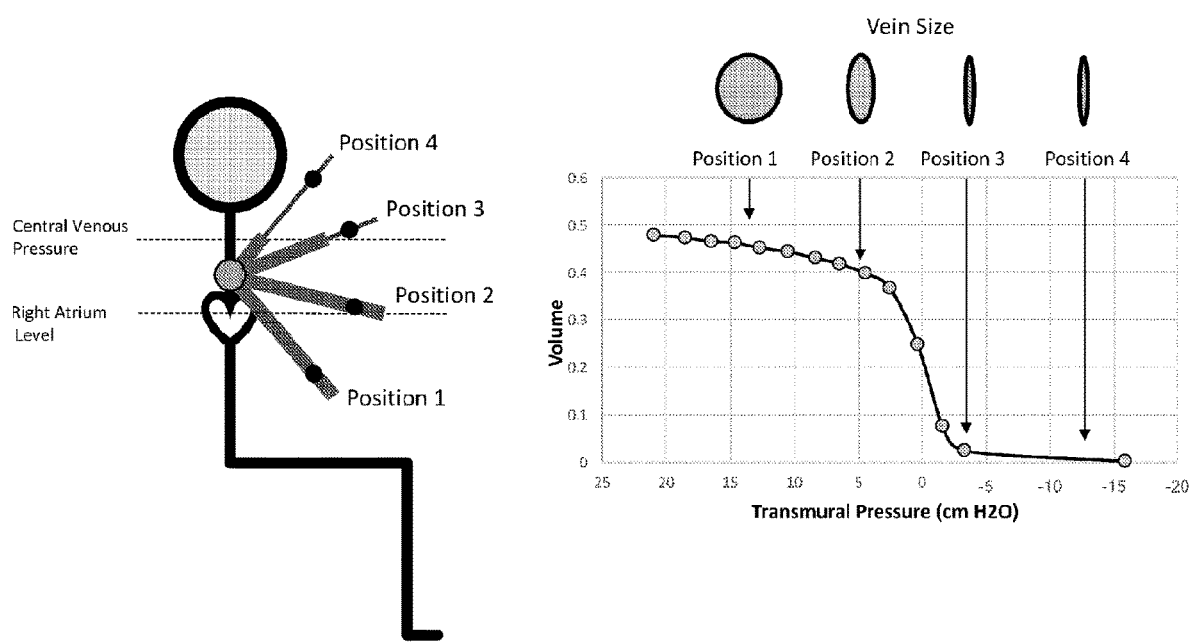
FIG. 6 is an illustration of venous volume change with an arm raise.

FIG. 6 is an illustration of the changes in transmural pressure and venous volume as the arm undergoes movement from a downward to upward position. An optical monitoring device is located for illustration purposes on the patient's wrist. When the arm is down (Position 1), the transmural pressure is quite high due to hydrostatic pressure created by the venous blood column. The veins are filled, with a circular profile, as demonstrated above the graph. At this position, venous volume is relatively insensitive to small changes in pressure due to positioning on the flatter portion of the distensibility curve. When the arm is moved close to more horizontal level (Position 2), the transmural pressure decreases due to the decrease in hydrostatic pressure. The vein size and venous volume decrease accordingly.

At Position 3, the optical sensing location on the arm has reached a height such that the transmural pressure is close to zero, and thus the veins will collapse. The peripheral venous pressure, and by continuity the CVP, is equal to the pressure at the point of collapse plus the pressure exerted by the vertical column of blood between this point and the right atrium. For example, if the point of collapse (zero transmural pressure) occurs 7 cm above the right atrial midpoint, then the CVP is 7 cm of blood (7.4 cm H2O). This vertical height is shown in the figure as the CVP pressure line.

As the arm is raised higher, for example to Position 4 in FIG. 6, the venous volume varies little because the veins are already in the collapsed state.

Physiological Realities

The above illustration presents a simplified and idealistic case for CVP determination. In reality, there are several nuances of human physiology and the measurement process that embodiments of the present invention mitigate for the accurate determination of CVP. These physiological complications and methodological challenges are described below.

Arterial Flow and Autonomic Changes

Figure 7:
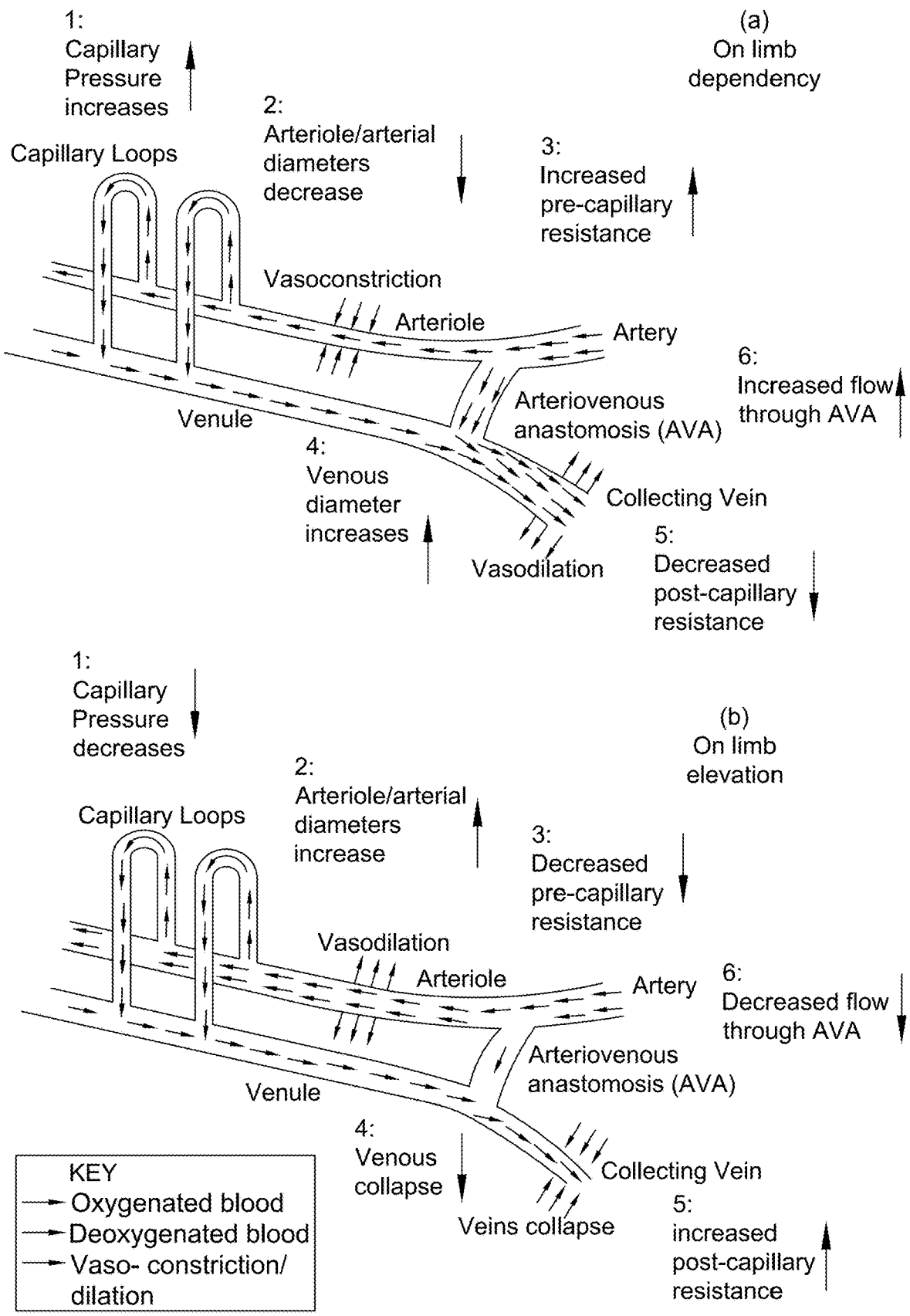
FIG. 7 is an illustration of physiological effects of arm raise.

Blood flow from the heart into the arm occurs in all arm positions. Since the system is a closed system, the amount of arterial blood into the arm must equal the amount of venous blood exiting the arm except for any changes in vascular size or change in volume. If one were to assume rigid tubing, the circulation through the limb in fact resembles flow through a u-tube siphon and flow through a rigid siphon is the same whether it is vertical, horizontal or upside down. If blood vessels were completely rigid, gravity would have no overall effect on the circulation. However, the system is not composed of rigid vessels and the autonomic system is actively involved in regulating flow through the arm. The vascular changes as well as autonomic changes have been characterized by Hickey et al. Hickey, M., Phillips, J. P., & Kyriacou, P. A. (2015). Investigation of peripheral photoplethysmographic morphology changes induced during a hand-elevation study. Journal of Clinical Monitoring and Computing. When the arm is down, capillary pressure is controlled by vasoconstriction resulting in increased pre-capillary resistance. The veins, however, are extended due to increased hydrostatic pressure. Additionally, in the end of the finger, there are numerous arteriovenous anastomoses that facilitate general blood flow through the arm and are directly involved in thermoregulation. FIG. 7, reproduced from Hickey et al., illustrates these changes in physiology. With the arm in the down position, vasoconstriction at the precapillary arterioles occurs to effectively reroute blood into the venous system through the arteriovenous anastomoses. In summary, when the arm is below CVP level, capillary flow is restricted, arteriovenous anastomoses flow is high and the veins are dilated. If a photoplethysmogram (PPG) is used to make optical measurements of the tissue, the AC (pulsatile) component of the signal will be small due to smaller arterial pulsations, while the DC (mean) absorbance of the signal will be increased due to the overall increase in blood volume in the tissue. As the arm is elevated, the autonomic nervous system seeks to maintain capillary flow and vasodilation occurs at the precapillary level. Flow through the arteriovenous anastomoses decreases. This physiological change occurs as the veins begin to collapse due to atmospheric pressure being greater than venous pressure resulting in a transmural pressure of zero. This collapse increases the systemic vascular resistance by decreasing the post capillary resistance. Thus, when the arm is above CVP level, capillary flow is increased, and the veins are collapsed. The AC component of the optical PPG signal will be larger while the DC absorbance component of the PPG signal will be decreased.

This complex array of physiological changes in the finger capillary bed creates a complex measurement environment for the determination of central venous pressure. If the PPG signal is obtained from the distal finger, as is the common location for pulse oximeters, the optical signal will be influenced by capillaries, the large number of arteriovenous anastomoses, and the veins. As photons travel in the tissue in a semi-chaotic manner due to scattering, they are not specific for any individual vascular compartment and a typical PPG measurement lacks any type of spatial resolution. This lack of defined spatial resolution limits the ability to isolate the vascular compartments. Thus, the distal finger is not a preferred measurement location for assessment of venous collapse.

The influence of autonomic changes due to arm elevation can be mitigated through selection of tissue locations where the number of arteriovenous anastomoses is reduced relative to the terminal tip of the finger and will facilitate measurement accuracy. Such locations include the base of the finger, back of the hand, and wrist.

Alternatively, the influence of autonomic changes due to arm elevation can be mitigated using optical measurement methods that have increased sensitivity for venous blood. These systems can include the incorporation of a spatially enhanced optical system, which is broadly defined as an optical system that improves specificity for venous blood volume changes. An example of such a system is the use of a reflectance PPG system that is placed directly over a vein. The resulting placement of the sensor improves the systems specificity for venous changes. Another example includes a low spatial resolution system containing, for example, multiple detectors that are located on the back of the wrist. Due to spatial differences in the wrist tissue, each detector will be sensitive to different contributions from arterial and venous sources. Based upon measured changes in the AC and DC signals or response profile to elevation changes, the detector with greatest specificity for venous volume can be selected. Alternatively, the signals from the multiple detectors can be used in combination and subjected to a blind source separation technique, such as independent component analysis, such that the venous signal source can be separated from the optical signals. Further spatial capability can be achieved by utilizing an imaging system that enables direct identification of veins. Such a system can process the images with vein identification and segmentation methods to isolate the signal to the venous compartments.

In addition to spatial capabilities, spectroscopic principles based upon the fact that deoxygenated hemoglobin and oxygenated hemoglobin absorbed differently can be used to facilitate blood compartment isolation. Pulse oximetry leverages these absorbance differences as well as the pulse or AC signal for determination of oxygen saturation. This general process can be effectively reversed for the isolation of the non-pulsatile venous component of the signal. The use of spatial techniques as well as vascular compartment techniques can be used to minimize physiological noise factors for the procurement of an accurate central venous pressure measurement.

Temporal Response Delay

A second physiological reality that embodiments of the present invention mitigate or compensate for is the fact that the vascular system does not have an instantaneous response to changes in transmural pressure, including hydrostatic pressure changes. If the arm is moved from a downward position to an upward position, the veins do not instantaneously collapse at a location above central venous pressure, as it takes time for the blood to move into the draining veins. The venous system is composed of varying diameter vessels with venous valves that prevent retrograde flow. These valves have an opening pressure as well as differences in compliance due to subject-to-subject physiological differences. The anatomical construct of the venous system results in a damped or delayed response that must be mitigated or compensated for such that an accurate measurement is obtained. Methods to minimize this influence will be discussed below.

Asymmetry Between Venous Emptying and Filling

An asymmetry between venous emptying and filling is an important element in the determination of CVP. Because venous valves prevent retrograde flow, veins must be re-filled from arterial flow, thus filling times will typically exceed emptying times. For example, as the arm moves from a lower position to an upper position, hydrostatic pressure changes are the dominant influence associated with venous collapse and emptying takes place over several seconds. However, if the arm is moved from an elevated position to a downward position, the veins do not become instantaneously distended because the venous capacity of the arm must be effectively refilled by arterial inflow. Upon moving the arm from a position to a down position, the time to fully refill the venous compartment in the arm can be on the order of 30 seconds, but will vary in accordance with vascular morphology and the current cardiac output. Therefore, when changing venous volume via transmural pressure changes, the directionality of volume change, emptying or filling, must be appropriately considered.

Influence of Contact Pressure

Most optical tissue measurements are performed by placing the optical measurement system on the tissue. The fact that the venous system is remarkably low-pressure, typically below 10 cm H2O (0.14 psi), requires careful attention that the optical system is not influencing the transmural pressure. If the optical system is placed in contact with the tissue, any impact on the venous transmural pressure must be effectively incorporated in the measurement methodology. The impact of localized transmural pressure changes can be minimized by utilizing a noncontact optical system. Such a system is designed to minimize any influence on transmural pressure and effectively determines venous volume in a noninvasive and nonintrusive manner.

Determination of Anatomical References

As noted previously, the ability to utilize jugular venous pressure as a method for central venous pressure determination is limited due to inter-operator variability largely associated with repeatable identification of anatomical landmarks as well as subject position. The accurate and repeatable determination of central venous pressure in a noninvasive and self-administered fashion requires the system to perform an assessment of anatomical landmarks, ensure appropriate positioning of the subject, or a combination thereof. If the central venous pressure measurement system is utilized for repeat measurements on a given subject, the system can use simple changes in the determined height level as the basis for comparison. In such a case, the repeatable positioning of the subject becomes an important parameter to control. If the system is to be utilized in a clinic setting with multiple patients, the system must determine anatomical dimensions in conjunction with determining the patient's body position. Systems and methods for addressing these issues are disclosed below.

Demonstration of Measurement Challenges

Figure 8:
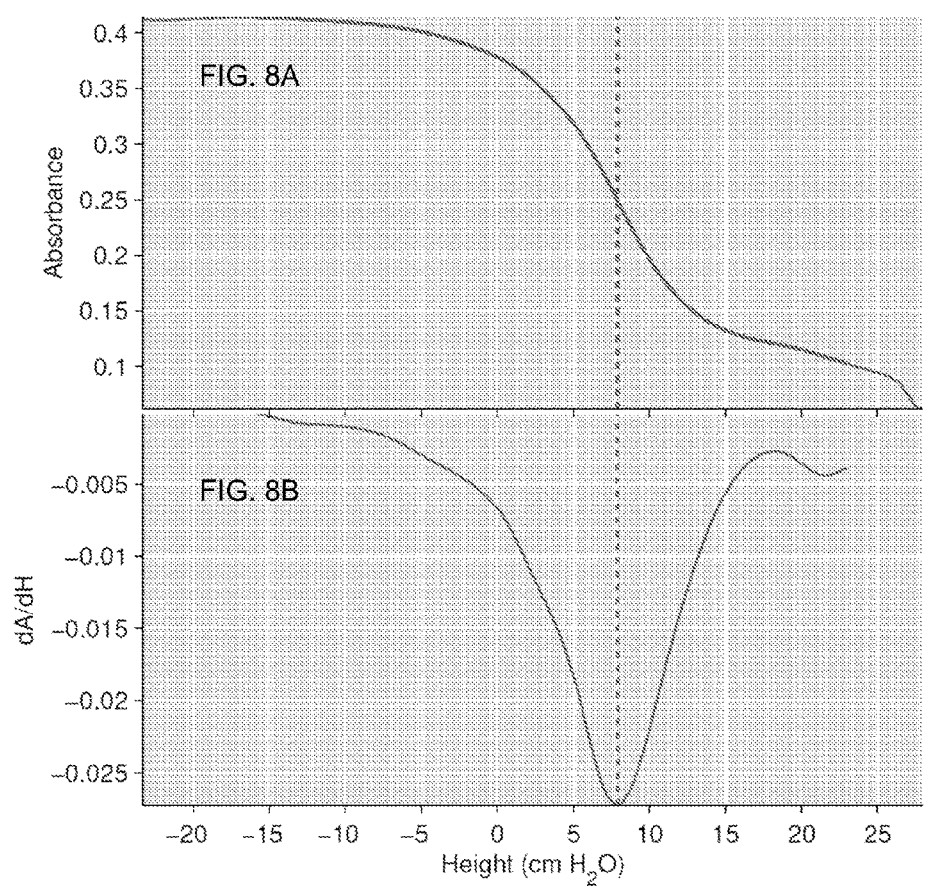
FIG. 8 is an illustration of using arm elevation to change transmural pressure.

The following examples illustrate the challenges associated with accurate CVP determination. In each example, PPG sensors were located on the wrist, and in some cases, the fingertip. For the wrist location, a lightweight PPG sensor was attached directly over a superficial vein using adhesive to minimize contact pressure. Transmural pressure change was achieved by raising the arm. FIG. 8A shows an example of PPG wrist data during slow arm raising. Initially, the change in optical absorbance is relatively flat with raising, however at roughly 0 cm H2O, relative to the suprasternal notch, the absorbance signal begins falls rapidly, marking venous collapse. The derivative of absorbance with respect to height is shown in FIG. 8B. The prominent negative peak in the derivative, denoted by the dashed line, marks the center of the transition from full to collapsed veins. The height at which the transition occurs will be related to peripheral venous pressure, and hence central venous pressure.

Terminal Finger Capillary Bed Difficulties

Figure 9:
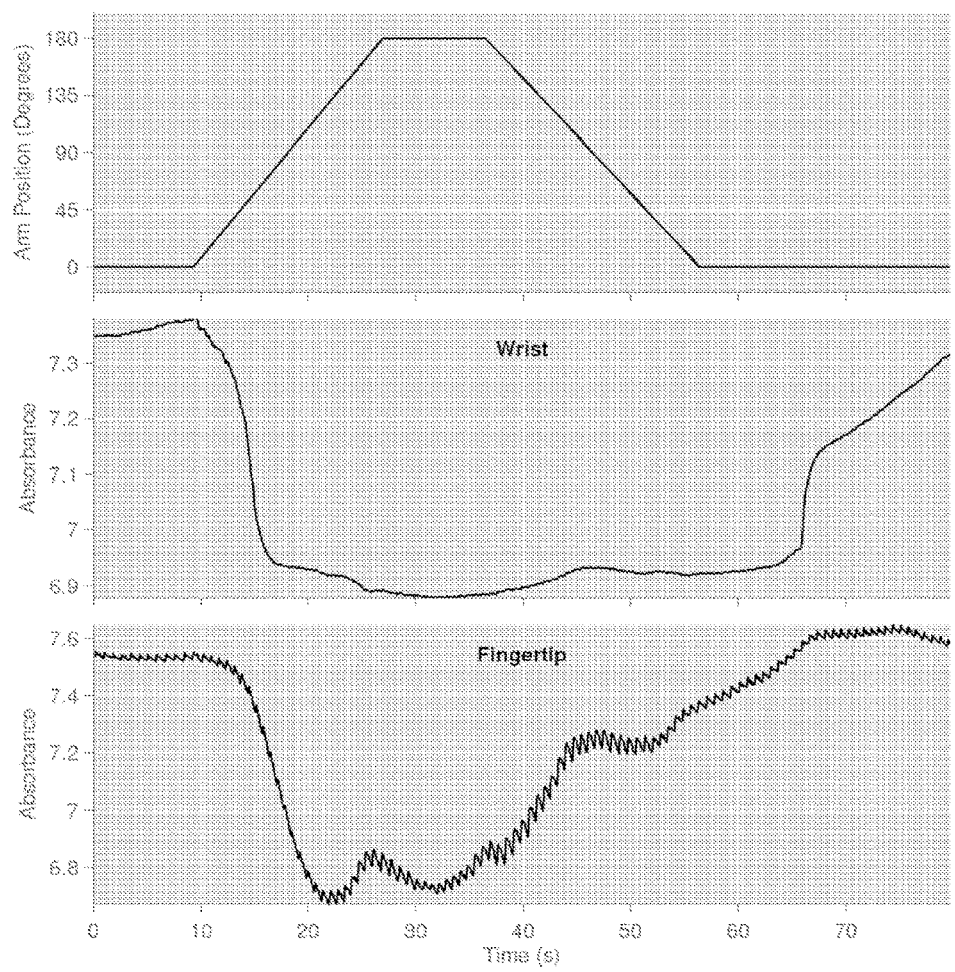
FIG. 9 is an illustration comparing tissue measurement sites.

FIG. 9 shows the complexity of using the terminal capillary of the finger as a sensor location. Optical absorbance signals at the terminal finger and at the wrist are shown as the arm is rotated from 0 degrees (straight down) to 180 degrees (up). The wrist shows the expected response with arm elevation: a decrease in absorbance that reaches a steady state once the veins have collapsed fully. In contrast, the fingertip location shows more complex patterns. There is an initial drop on absorbance due to increase in arm elevation, however a steady state is not reached due to the large influence of autonomic arterial vasodilation which is apparent from the increased AC (pulsatile) component of the signal. The overall blood signal reaches a nadir at roughly 22 seconds, but then undergoes fluctuations due to the opposing responses of venous and arterial systems.

External Pressure Sensitivity

Figure 10:
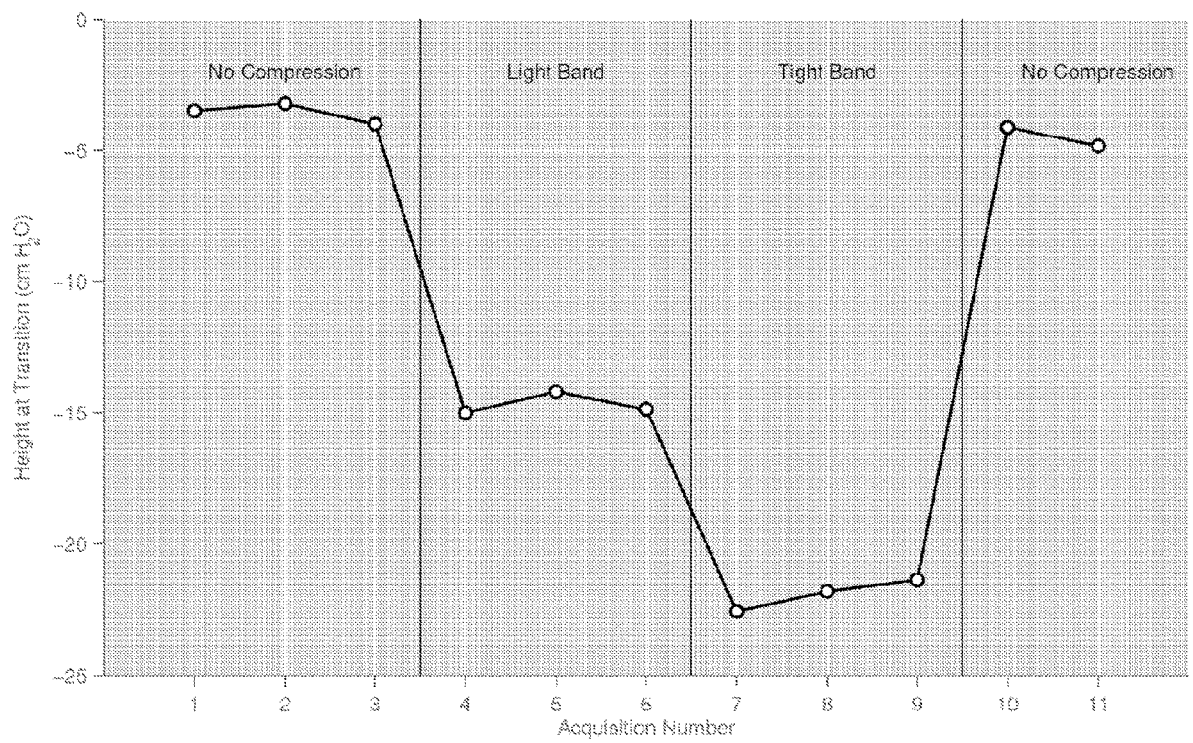
FIG. 10 is an illustration showing the influence of pressure on the measurement site.

FIG. 10 shows the substantial impact of contact pressure on the determination of peripheral venous pressure during an arm elevation experiment. When very light contact compression was added around the PPG sensor, the pressure of venous collapse was decreased by more than 10 cm H2O due to the decrease in transmural pressure. Tightening the band on the PPG sensor decreased the point of venous collapse further.

Rate of Height Change Sensitivity

Figure 11:
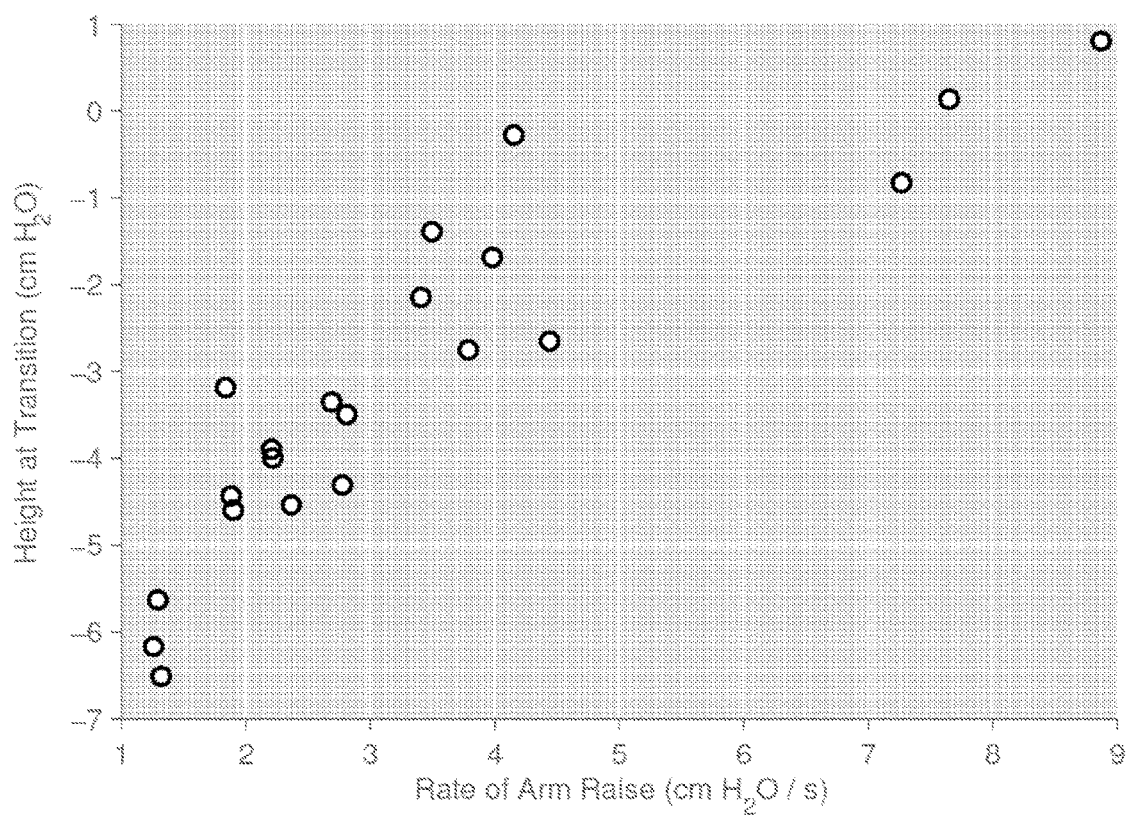
FIG. 11 is an illustration showing the impact of the rate of transmural pressure change.

Venous emptying and collapse are not instantaneous processes, hence the rate of arm movement or the speed of transmural pressure change is a variable that must be compensated for or otherwise controlled. FIG. 11 shows that the detected height of transition is dependent on the rate of arm movement. Because of the time required for venous collapse, faster movements will result in less accurate CVP determinations.

Venous Response is Not Symmetric

The volume in the venous system does not respond symmetrically to arm raise and arm lowering, as can be seen in FIG. 9. For both the wrist and fingertip, the change in absorbance upon raising the arm is fast. However, the response to arm lowering is much slower, as the venous compartment must be refilled. At the wrist location, the absorbance signal does not return to baseline values until more than 20 seconds after the arm has return to the downward (0 degrees) position.

General Measurement Methods

Optical Measurement System

The optical measurement system can take many forms, from a single source and detector configuration to a multiple wavelength/multiple sensor configuration. For purposes of illustration, four measurement systems will be described.

Figure 12:
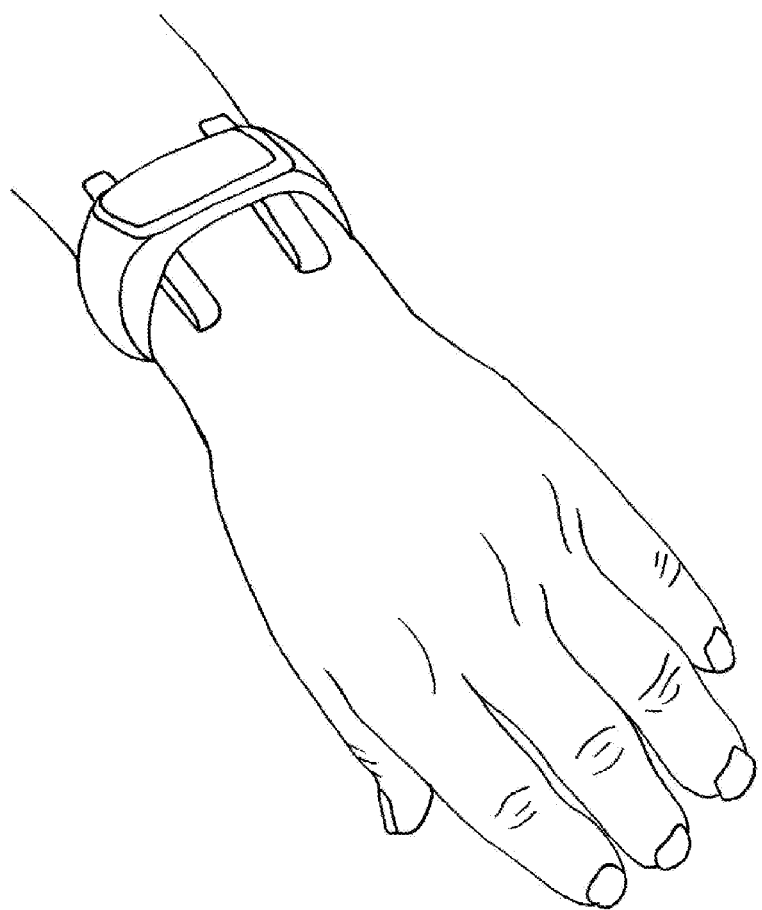
FIG. 12 is an illustration of wrist-mounted sensor system.

One system for determining venous volume involves positioning several optical sensors beneath a wrist-based device. The sensing system can be attached to the wrist in a manner that the area beneath the sensors is not in physical contact with the device. Measurement algorithms can then be used to determine which sensor or combination of sensors provides the best information associated with venous volume change. FIG. 12 is an illustration of such a system.

Figure 13:
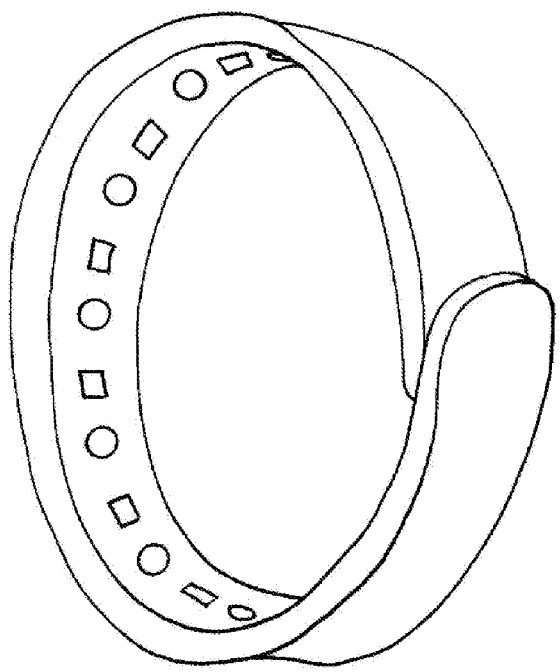
FIG. 13 is an illustration of a bracelet measurement system.

A second measurement system includes a bracelet that contains LED-detectors around the entire circumference of the device. At any point in time, some of the sensors will be in contact with the tissue thus procuring a traditional PPG signal. The remaining sensors will be close to the tissue but not in contact and can be used for determination of venous volume. The combination of concurrent PPG information with venous volume information at one or more wavelengths creates a system that enables arterial influence compensation. FIG. 13 is an illustration of such a system, where circles denote LEDs and squares denote photo-detectors.

Figure 14:
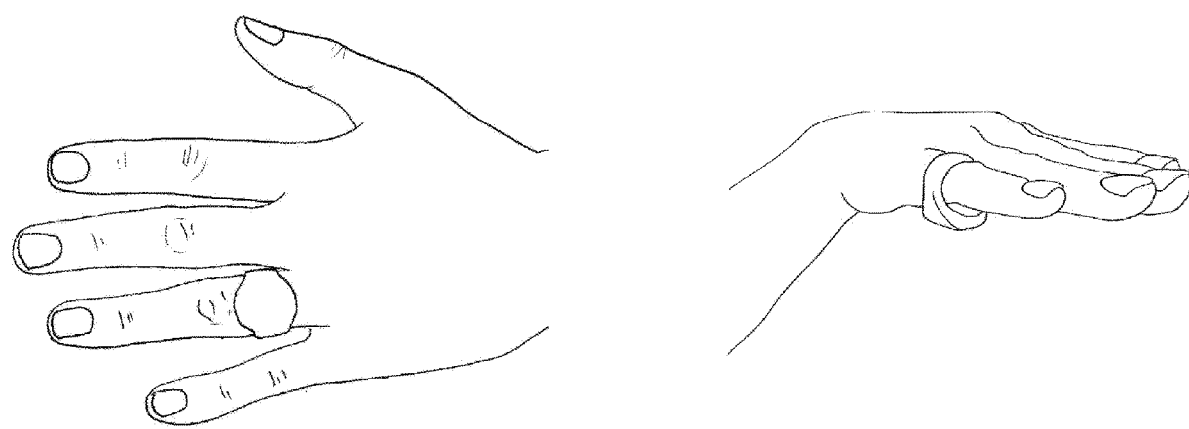
FIG. 14 is an illustration of a base of the finger based measurement system.

A third measurement system is ring based for use at the base of the finger. Such a system can include a singular source and detector relationship, or can include many sources and detectors located around the circumference of the ring. Such a system can acquire data from multiple source detector configurations for the procurement of both arterial and venous signal information. FIG. 14 is an illustration of such a system. The figure shows a possible use scenario where the ring is located on the ring finger for general cardiovascular monitoring while CVP measurement can occur by placing the ring on a small ringer with the sensors not in contact with the tissue. This is effectively a non-contact PPG system.

Figure 15:
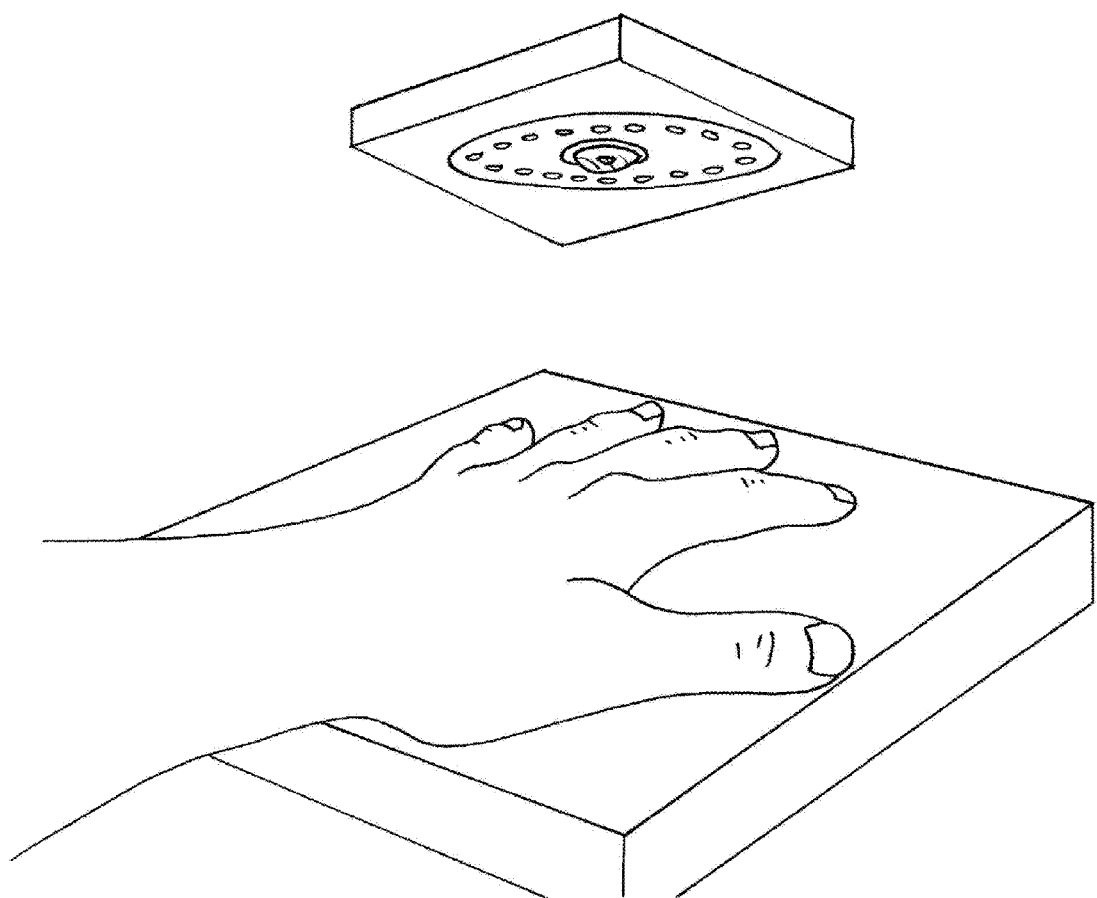
FIG. 15 is an illustration of a vein imaging system.

A fourth measurement system can comprise a camera for doing direct vein imaging. Such a vein imaging system can be configured to include an LED ring composed of infrared light emitting diodes that have some specificity for venous blood. One such wavelength can be 850 nm. Imaging can use reflectance illumination, which will weight the optical signal toward superficial veins; trans-illumination, which passes light through the entire finger or hand; or a combination of reflectance and trans-illumination. When used in reflectance mode, the illumination can be polarized with subsequent cross polarization prior to optical signal detection to remove specular or front surface reflections. The camera can be sensitive to the infrared light and can contain additional filters or processing algorithms to effectively remove ambient light conditions. Such a system can be modified to enable operation as a polarization difference imaging system. FIG. 15 is an illustration of such a system.

Alternatively, changes in venous volume can be measured with a multispectral imaging system that provides greater specificity for venous blood. Such an imaging system uses narrow-band illumination at multiple wavebands and a camera capable of acquiring multi-spectral images. A suitable imaging system can include illumination with narrow-band LEDs centered at red (660 nm), green (550 nm) and blue (450 nm) wavelengths, combined with a commercial RGB camera that can simultaneously acquire three images with differential specificity for red (R), green (G), and blue (B) illumination. Illumination can utilize orthogonally oriented polarizers to reduce specular reflections. Such a system has been demonstrated by Jakovels and Spigulis to measure changes in venous volume. Jakovels, D., & Spigulis, J. (2012). RGB imaging device for mapping and monitoring of hemoglobin distribution in skin. Lithuanian Journal of Physics, 52(1).

The actual measurement of venous volume as observed by the optical system can take a variety of forms. The determination of venous volume can be made using standard absorbance spectroscopy measurements where the absorbance of the blood is proportional to the path length. Additional methodologies can be based upon the width of the vessel or the height of the vessel.

Intravascular Changes in Transmural Pressure

Intravascular pressure changes can be accomplished by multiple methods. Hydrostatic pressure changes can be created by multiple means including arm elevation changes. Elevating the arm reduces the pressure by approximately 0.77 mmHg $cm^{-1}$ of vertical displacement from the heart (Gavish and Gavish 2011), while lowering the hand increases the local arterial pressure by the same factor.

Figure 16:
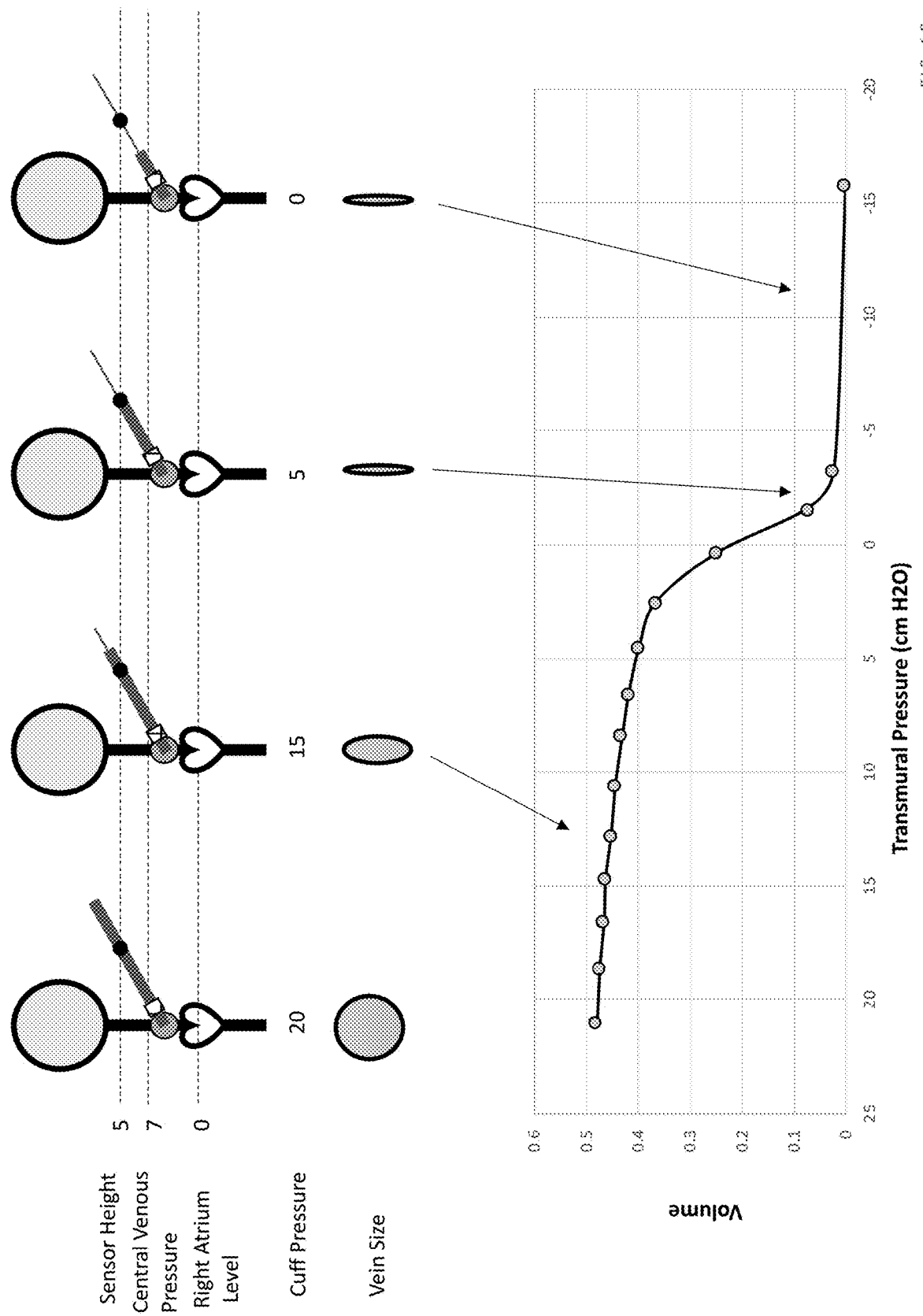
FIG. 16 is a schematic illustration of the use of an external cuff to modify transmural pressure.

Intravascular venous pressure can also be altered by modifications made at more proximal locations, i.e., closer to the heart. FIG. 16 is an illustration of such a system in use. In the example, the patient has a CVP of 7 cm H2O. The sensor is located at a height of 12 cm above the right atrium. In the left most figure, the external cuff is inflated to 20 cm of H2O. In this condition, the transmural pressure has been increased such that the location of venous collapse (0 transmural pressure) is at 20 cm H2O, which is above the senor location. The vein at the sensor site is fully filled as depicted in the figure. At a second point in time, the cuff pressure is decreased to 15 cm H2O. The location of venous collapse has decreased to 15 cm H2O, but this remains above the sensor height at 12 cm H2O. As the pressure in the cuff is decreased, the height associated with transmural pressure of zero will decrease until venous collapse occurs below the optical system. In the illustration, this occurs at a pressure of 5 cm H2O. Cuff pressure decreases below 5 cm H2O would show little changes due to the fact that the vein is largely collapsed. An important element of this measurement protocol is that the pressure in the cuff is not reduced until the venous volume has equilibrated. The method described does not require arm movement and creates a method for systematically and easily determining central venous pressure.

An additional method for varying transmural pressure is to use intrathoracic pressure variance to create transmural pressure changes. However, the need to breath at a reasonable rate necessitates that these changes in intrathoracic pressure be time varying. The use of time varying signals has benefits due to the ability to isolate the signal in the frequency domain. Venous return to the heart can be systematically altered by changing intrathoracic pressures. Guyton venous return curves demonstrate this physiological relationship well. The use of a resistance breathing protocol creates negative and positive intrathoracic pressure changes. FIG. 17 and FIG. 18 illustrate the use of this concept for CVP determination. In FIG. 17A, the arm is elevated to a level such that changes in intrathoracic pressure have little influence on venous volume. As illustrated, only the maximal intrathoracic pressure resulting in maximal transmural pressure initiates filling of the vein. 1701 illustrates a point of maximal intrathoracic pressure. Maximal intrathoracic pressure, results in maximal transmural pressure thus resulting in partial venous filling. As illustrated, the overall optical signal variance will be quite small.

As shown in FIG. 17B, the overall height of the arm is decreased such that the sensor is now located at central venous pressure. The same degree of intrathoracic pressure as noted by 1702, now results in a more complete filling of the vein and a corresponding larger change in the absorbance signal. As illustrated, the changes in intrathoracic pressure now create a variance in venous filling from a collapsed vein to a partially filled vein. The resulting optical variance is therefore increased.

FIG. 18A illustrates a further reduction in arm height such that the sensor is now located at a height slightly below central venous pressure. Changes in intrathoracic pressure due to resistance breathing create negative and positive changes in intrathoracic pressure around the normal intrathoracic pressure. The resulting excursions in intrathoracic pressure create additional transmural pressure variances that result in a maximum level of blood volume change with the transmural pressure is approximately zero. Specifically, the vein transitions from a collapsed state due to negative intrathoracic pressures due to inhalation, and a filled condition due to positive pressure exhalation. FIG. 18B illustrates an additional lowering the arm such that the changes in intrathoracic pressure do not result in venous collapse. The resulting optical signal has decreased variance as the vein under examination remains nominally filled.

One of ordinary skill in the art will appreciate that transient changes in intrathoracic pressure due to resistance breathing, mechanical ventilation, Valsalva maneuvers, Mueller maneuvers, and other perturbations that change venous return to the heart can be utilized to create variances such that central venous pressure can be determined.

Extravascular Changes in Transmural Pressure

Changes in the transmural pressure across the vein can be achieved by changes in the external pressure. An example of such an external pressure change is the placement of the arm in a water bath, static pressure or physical compression of the vein by a physical object. These types of external pressure application are consistent with physical tonometry. Given the very low pressure resident in the venous system, conventional physical tonometry does not lend itself well to self-administration due to the very high level of precision that is required. An important element of some embodiments directed toward this application is the use of noncontact tonometry. In noncontact tonometry, the force used to create transmural pressure changes is dynamic (velocity) pressure, static pressure, or a combination.

Dynamic pressure is the result of changes in direction and velocity of air flow. In a dynamic pressure system, the velocity and the resulting force (pressure) can be controlled to increase the pressure on the skin surface, which contains superficial veins. At the point of venous flattening, the pressure exerted by the air column at that moment is recorded and converted into mmHg. This pressure represents a point where the transmural pressure is zero. Based upon subject anatomical measurements in conjunction the height of the heart relative to the sampling location, a central venous pressure can be determined. In practice, the air column utilized for generating the applanation force is large enough to exert pressure on multiple veins within a defined area. The area of constant force can be effectively imaged for the determination of venous volume changes.

Changes in transmural pressure can be achieved by using static pressure changes. Static pressure is the measure of the potential energy of a unit of air. For example, air pressure on a duct wall is considered static. Imagine a fan blowing into a completely closed duct; it will create only static pressure because there is no air flow through the duct. A balloon blown up with air is a similar case in which there is only static pressure. The described system uses mostly static air pressure, as there may be some air loss. If the hand or skin location is subjected to changes in the external or surrounding air pressure, the result is a change in transmural pressure. In practice, changes in external or surrounding air pressure can be created by placing the hand in an enclosure with some degree of air flow restriction. If the volume of air entering the chamber exceeds the volume existing, then the pressure increases. This process can be used to create a controlled pressure environment that is insensitive to the subjects hand size and other anatomical differences.

Figure 19:
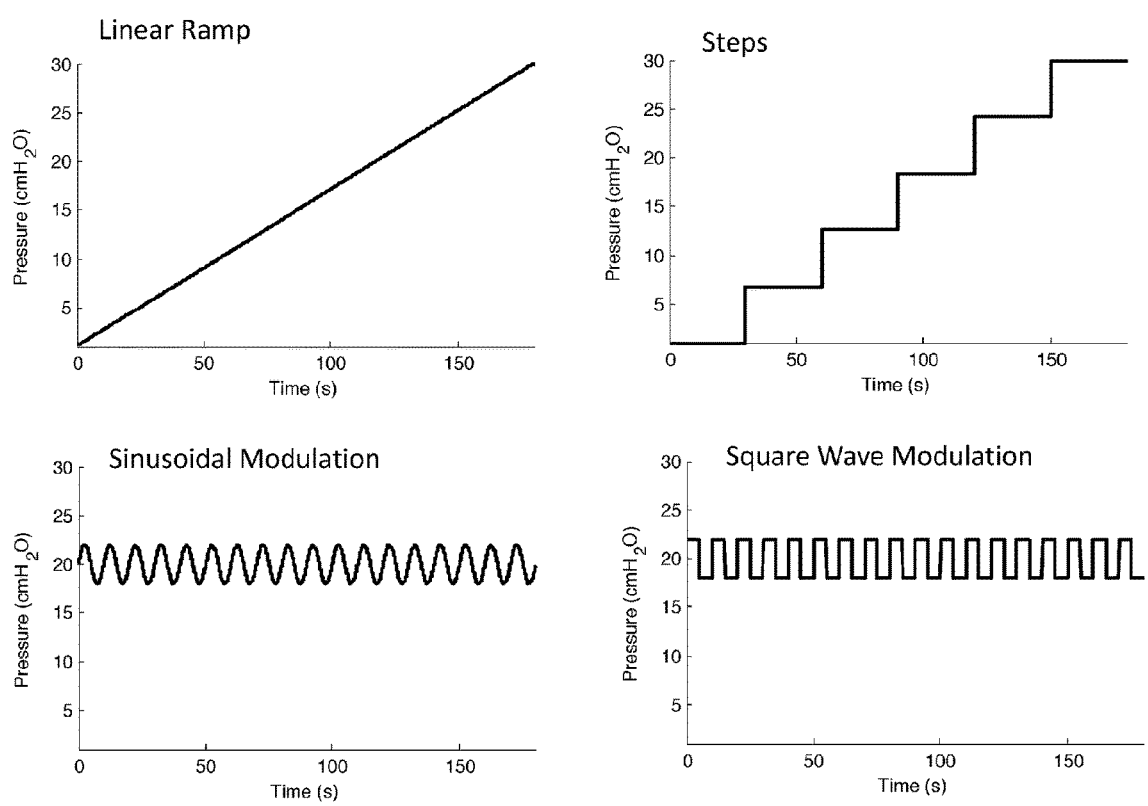
FIG. 19 shows examples of pressure profiles used to vary transmural pressure.

For both dynamic and static pressure systems, a variety of pressure profiles may be implemented that yield determination of the peripheral venous pressure, and hence central venous pressure. These include, but are not limited to, any combination of ramps, steps, or periodic modulations in pressure. FIG. 19 shows examples of pressure profiles that can be used to change transmural pressure. In one use scenario, the pressure can be linearly ramped from low to high values and the collapse pressure is determined as the pressure point where the venous volume underwent the largest change (i.e., minimal temporal derivative). Alternatively, the pressure can be increased in discrete steps, where the duration at each step is sufficiently long to ensure that the venous volume has stabilized to a steady-state value. In this case, the collapse pressure can be determined as the midpoint pressure between steps that creates the largest decrement in venous volume. To avoid discretized values limited by the pressure step size, parametric or non-parametric curve fitting tools can be used to interpolate the relationship between mid-point pressure and venous volume, resulting in a refined estimate of the collapse pressure. Note that ramps or steps can also descend from high to lower pressure, however due to the temporal asymmetry between venous emptying and filling, it can be preferable to increase pressure and empty veins rather than to decrease pressure and wait for venous filling.

Periodic modulations, for example sinusoidal or square wave patterns, can also be used to determine peripheral venous pressure. Periodic modulations can offer an advantage because they isolate the signal of interest to a specific frequency band. This is important, because venous volume can undergo significant changes related to breathing and vasomotor tone (i.e., vasoconstriction and vasodilation) mediated by sympathetic innervation and local physiology. By modulating pressure at a specific frequency and using Fourier-based or other analysis methods intended to enhance or isolate signals within specific frequency bands, the sensitivity to these confounding noise sources can be decreased. In a typical use scenario, relatively small pressure modulations (AC component) are used in combination with slow pressure ramps or steps (DC components) to create an effective pressure profile, shown in FIG. 20A. When the DC pressure component is low and below the peripheral venous pressure, the AC pressure change will produce relatively small changes in venous volume. When DC pressure reaches the peripheral venous pressure, the transmural pressure will become zero, and the AC modulation will produce large changes in venous volume. When the DC pressure is above peripheral venous pressure, the AC component in venous volume will again be small as the veins are collapsed. These effects are illustrated in FIG. 20B, which shows the changes in venous absorbance due to pressure modulations. Thus, peripheral venous pressure can be identified as the DC pressure value where AC pressure modulations produce the largest changes in venous volume.

The depth of the veins relative to the surface of the tissue as well as skin elastic properties can create measurement variances. If an objective of the system is to measure venous pressure and not skin elasticity, variances in skin elasticity can be considered a noise source. Such variances in the skin elasticity can be effectively compensated for utilizing leveraging techniques used in the intraocular pressure measurement arena. Specifically, differences in corneal thickness are unknown source of intraocular pressure variance. Differences in corneal thickness have been effectively compensated for by using hysteresis calculations or ocular response analysis. The ocular measurement system uses a column of air of increasing intensity as the applanating force. The ocular response analyzer notes the moment of applanation, but the air column continues to emit with increasing intensity until the cornea is indented. The force of the air column then decreases until the cornea is once again at a point of applanation. The difference in the pressures at the two applanation points is a measure of the corneal elasticity (hysteresis). Mathematical equations can be used to "correct" the applanation point for high or low elasticity. This "corrected" intraocular pressure is less dependent on corneal thickness. Although intraocular pressure measurements utilize a reflectance angle and thus are significantly different than the current system, the inventors have discovered that using the underlying concept of utilizing increasing and decreasing pressures can be used to improve the accuracy of venous pressure determination. For the purposes of venous pressure determination, the method works by creating a force on the object until a defined compression of the vessel has occurred. The application of air pressure is continued beyond this point and slowly withdrawn until a similar observation is obtained. The difference in the two pressures (forces) at the two defined measurement points is a measure of skin elasticity (hysteresis). This information enables the use of mathematical calculations to correct for the influence of the skin.

Anatomical Measurements

The determination of anatomical measurements by a clinician or other care provider has been historically error-prone due to differences in measurement technique. To alleviate these measurement technique differences, embodiments of the invention use optical recognition techniques for the determination of critical anatomical measurements. Anatomical measurements can be performed by optical systems using structured light or 3-D camera systems. Multiple substantiations of such systems exist; currently available systems include the MICROSOFT KINECT, ORBBEC ASTRA, INTEL REALSENSE, and STEREOLABS ZED stereo camera. These systems operate by different principles but are able to make measurements in 3-dimensional space. Multiple systems are capable of skeletal tracking that captures the "skeletal" location of the subject including hands and fingers. Han et al. present a comprehensive survey of existing space-time representations of people based on 3D skeletal data, and provides an informative categorization and analysis of these methods from the perspective of information modality, representation encoding, structure and transition, and feature engineering. Han, Fei, et al. "space-time representation of people based on 3d skeletal data: a review." arXiv preprint arXiv:1601.01006 (2016).

The image capture system allows appropriate location of joints and measures distances between them and can be used for determining the position of the subject in a specific plane. In practice, the system maps the environment where the evaluation takes place, tracks the position of the subject in this environment, and maps the subject's joints for the construction of a skeleton. The resulting skeleton can be used for determination of anatomical measurements as well as determining the three-dimensional position of the body. Such information can be augmented by face detection to include the exact location of the subject's eyes. Eye location in combination with overall body position creates a powerful tool for ensuring that the subject is appropriately positioned for determination of CVP.

Sensor Height Measurement

In several example embodiments, it can be desirable to determine the location of the sensor relative to the ground, heart or other defined reference point. The process of determining sensor location can be done via a measurement system that is attached to the subject (discussed below) or by observing the subject. The structured light or 3-D camera system described above for the determination of anatomical dimensions can also be used for the determination of sensor location. Additional methods include the use of motion capture systems involving an external camera for scene capture and markers placed on the subject. Optical-passive techniques use retroreflective markers on the vein sensor can be tracked by the camera. Optical-active techniques use LED markers. Both methods can be easily implemented by including markers or light emitting diodes, etc. onto the venous sensing system.

Attached Height Position Systems

The ability to determine the location of an object on the finger, hand or wrist can be enabled via an inertial measurement unit (IMU) system. A typical IMU system containing accelerometers and gyroscopes can measure the angular positioning of an object in 3D space, which can be used to estimate the position of the object under conditions of controlled movement, such as an arm swing. Additional accuracy can be achieved by using an IMU in combination with a camera. Several variances exist on this approach, but the best known is TANGO (formerly named PROJECT TANGO in testing). TANGO is a technology platform developed and authored by GOOGLE that uses computer vision to enable mobile devices, such as smartphones, tablets and watches to detect their position relative to the world around them without using GPS or other external signals. PROJECT TANGO is able to determine a device's position and orientation within the environment. The software works by integrating three types of functionality: (1) motion-tracking: using visual features of the environment, in combination with accelerometer and gyroscope data, to closely track the device's movements in space, (2) area learning: storing environment data in a map that can be re-used later, shared with other PROJECT TANGO devices, and enhanced with metadata such as notes, instructions, or points of interest and (3) depth perception: detecting distances, sizes, and surfaces in the environment. Together, these generate data about the device in "six degrees of freedom" (3 axes of orientation plus 3 axes of motion) and enable the position of the device to be known in absolute coordinate space.

Note that if only relative position, rather than absolute position, is necessary, accelerometer and gyroscope data from an inertial measurement unit (IMU) can be used to approximate the angular movement and displacement of the system.

Additional height sensing systems can include the use of Lidar. Many implementations are possible; one example system has the lidar system mounted in a gimbal, so it is focused on the ground, whereas another example has the lidar system effectively spinning in the vertical plane so it could determine the distance between the floor and ceiling. Additional distance detecting systems, including ultrasonic systems, infrared systems and time-of-flight measurement systems can also be suitable.

Determination of Height Difference Between the Heart and Peripheral Vein

Figure 21:
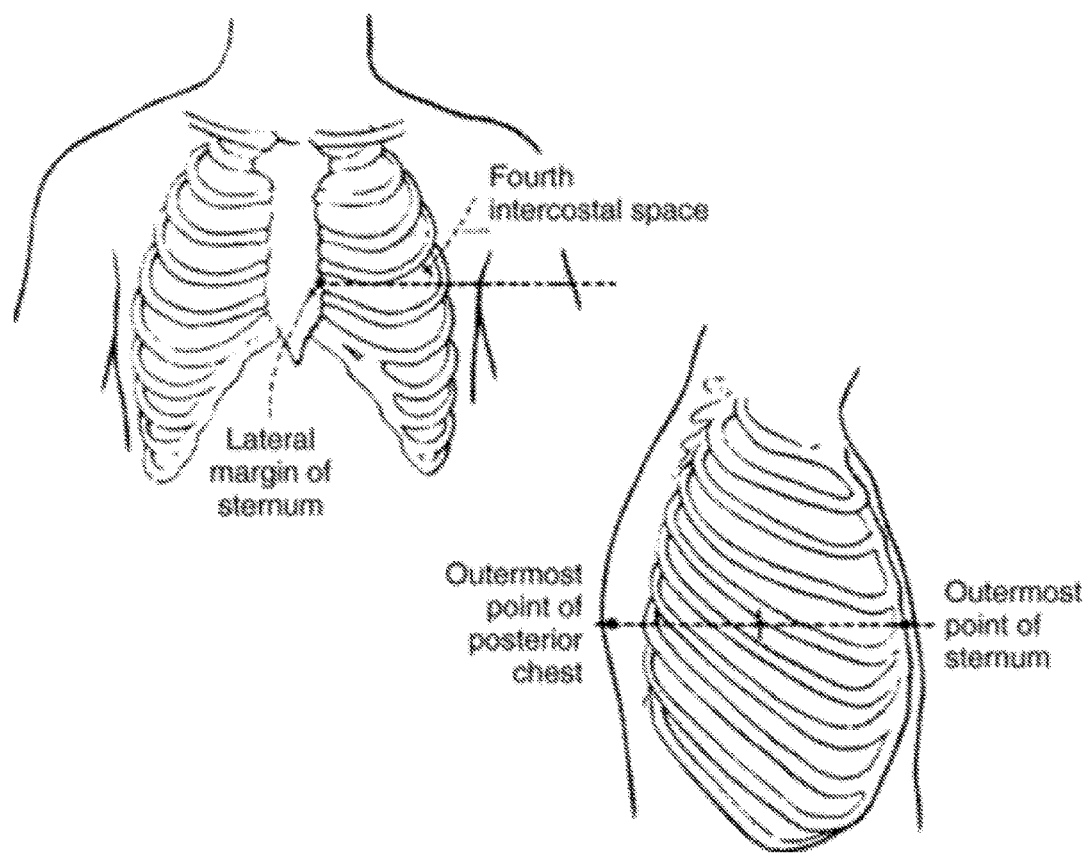
FIG. 21 is an illustration showing the location of the phlebostatic axis.

For the measurement of CVP using a peripheral vein location, the height relationship between the measurement location and the right atrium relevant landmark must be determined. The location of the right atrium within the thoracic cavity is difficult to determine due to size differences between people, and the lack of visible landmarks. As measured today, a trained medical professional determines the location of the heart by palpating for anatomical landmarks. The phlebostatic axis is the approximate location of the right atrium, and is found at the intersection of the midaxillary and a line drawn from the fourth intercostal space at the right side of the sternum, as shown in FIG. 21. Historically, the determination of right atrial location has been error prone due to anatomical variation, palpation errors, and differences in measurement techniques.

Figure 22:
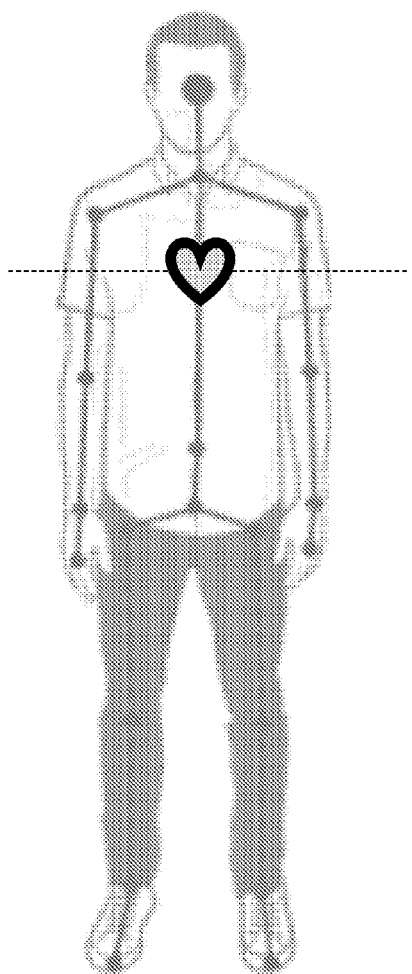
FIG. 22 illustrates the identification of anatomical measurements from an image of a subject.

Embodiments of the invention provide a simpler method for heart location determination using imaging and modeling techniques that do not require medical training or direct palpation. The subject's anatomical measurements are obtained by having the subject stand near the instrument. Images of the subject are acquired and image processing and skeletonization procedures enable determination of key anatomical measurements such as but not limited to torso length, limb length and neck length, as shown in FIG. 22. Established ratios are used to define the relationship between limb length, torso length and right atrial location. Data sources that can be used to define these ratios include information sources that include externally observable limb information with corresponding heart location information, for example MRI, CT scans, and X-rays. Segmentation of data sources by subject characteristics, such as ethnicity, and gender, can further refine ratios to improve the estimate of right atrial location. The result is an estimated heart location relative to visible landmarks and skeletal features as the person stands in front of the camera. The determination can be made with a conventional camera or a 3-D camera.

Figure 23:
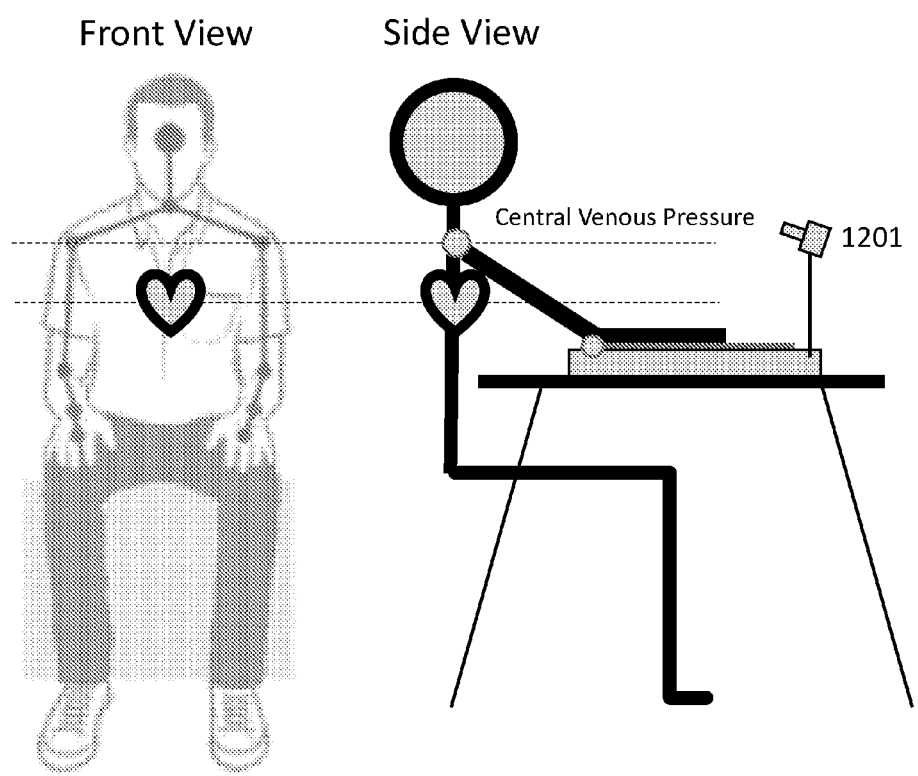
FIG. 23 illustrates the identification of the location of the heart using optical methods.

To obtain a CVP measurement, the subject sits at the table, as shown in FIG. 23. Thus, the heart location obtained via optical assessment can be translated or maintained as the subject moves to the seated position. The camera located on the device is used to assess the heart location as the subject moves into the seated position. The system can use visible landmarks such as the sub-sternal notch, joint locations, or physical objects such as head and shoulder to determine the location of the heart. With identification of the heart location on the subject, the system can determine the height between the measurement location and the heart. This method can be used in the ambulatory clinic setting or the home setting for the determination of central venous pressure. This method can be augmented by processes defined for repeatable positioning of the heart.

Determination of Relative Heart Position for Repeated Measurements

For repeat measurements, it is desirable to reproduce the height relationship between the measurement location and the heart, or determine changes from previous measurements with an accuracy of 1-2 cm. Given the number of articulated joints in the human body, such a repositioning task has many nuances and appreciable complexity. For example, consider the following scenario. The subject uses the same rigid chair and the same table for testing, but the subject is leaning forward. The angular displacement of the torso creates a lower heart height relative to a previous measurement when the subject was sitting in a vertical position. Similarly, leaning to the side or simply slumping in the chair can cause the heart location to move by several centimeters. The process of accurately repositioning the height of the heart or determining the extent to which the heart has moved is further complicated by the fact that the heart is not located on an externally visible surface but rather exists within the variably sized thoracic cavities.

Heart repositioning can be achieved by having the body occupy the same volumetric space as an initial or prior measurement. If the body is in the same volumetric space, then the heart is effectively in the same exact location and repeatability of heart height has been obtained. Optical measurement systems with depth capabilities can be used to ensure volumetric space alignment of the torso or upper body. Multiple baseline measurements can be made with the body in various positions. If a subsequent measurement satisfies the volume match requirements a measurement can be made. Volumetric matches can be determined based on joint locations, body edges, or alignment of other physical objects.

Figure 24:
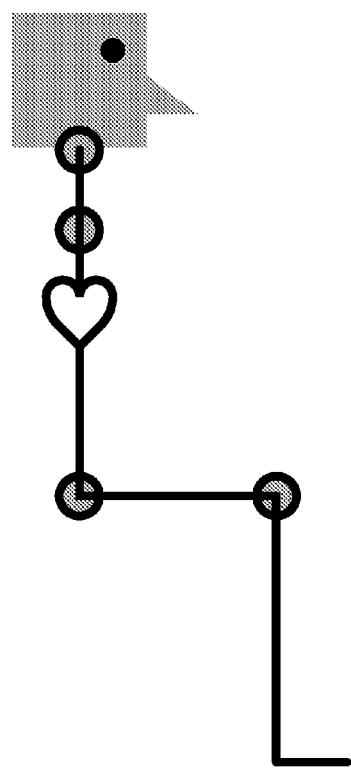
FIG. 24 is an illustration of a linkage model of human anatomy.

The volumetric matching process can be affected by differences in external clothing, which can place restrictions on the type and amount of clothing used by the subject. To alleviate possible clothing restrictions, the system can use the position of the head as a location tool. The method can be based upon modeling the seated subject as a series of linked objects with ball socket connection points. The first link is the attachment to the chair with subsequent linkages extending upward. As shown in FIG. 24, the system is modeled as two major linkages above the chair, back and neck, with the head attached to the top linkage. In such a model, the non-vertical alignment of any linkage results in a decrease in height of the head position. Thus, relocation of the head in a maximal position requires that the linkages be vertical. Thus, the obtainment of a repeatable head position can be used to create a repeatable heart height location. However, the determination of head position is difficult because the head has multiple degrees of freedom. Additionally, the face of the subject is anterior to the axis of the spine and neck. This asymmetry is noted and addressed in the solution provided.

Figure 25:
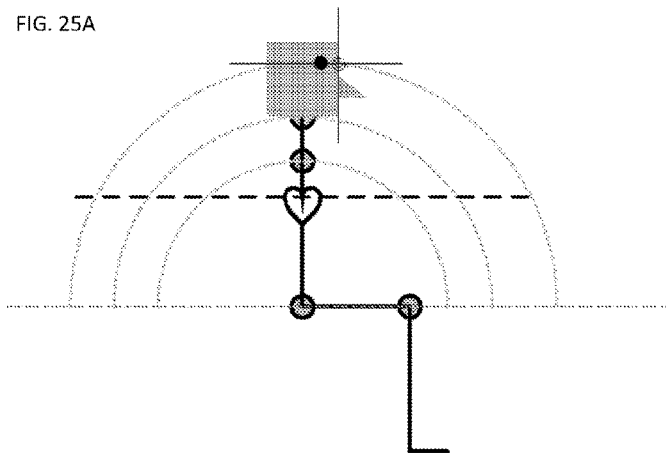
FIG. 25 is an example of subject repositioning using head position.
Figure 25:
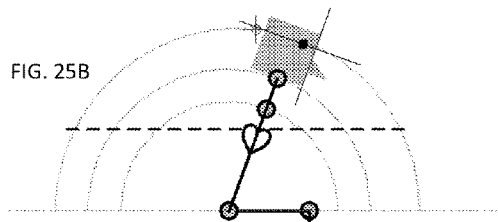
Figure 25:
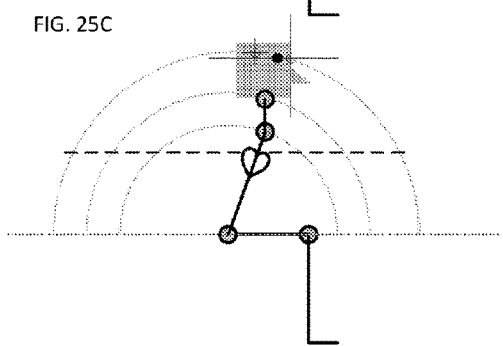
Figure 25:
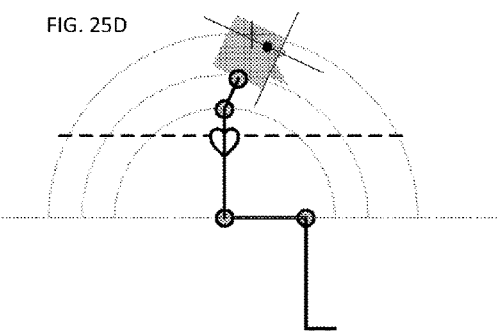

FIG. 25A illustrates the subject in a vertical position and defines a 3-axis coordinate system using the pupil level, a vertical axis on the face and a horizontal axis. Many coordinate systems can be defined, and the following is used for illustration purposes. In FIG. 25B, as the subject bends forward while maintaining back-neck-head alignment, the coordinate system rotates forward, and the intersection point defined by the coordinate system moves to a lower height. FIG. 25C shows a situation where the subject bends forward but has the neck and head vertically aligned. In this case the axis system is not rotated but the intersection point is at a lower height. FIG. 25D shows a situation where the heart is at a maximum height, but the head axis has rotated, and the intersection has decreased. Such a scenario defines a situation where the subject position is different, but heart height has been maintained. In practice, the subject can raise their head and straighten their neck such that full alignment is achieved. FIG. 26 illustrates that the method maintains functionality in the presence of lateral or tilt movements of the body.

As illustrated in the prior figures, head position can provide a key element for obtaining a repeatable body position since it represents the end of the linkages and is typically not covered with clothing. The orientation of the head as defined by roll, pitch and yaw, plus the height of the head or the height of a defined axis intersection can be the basis for head position determination. A single axis or single reference point determination can result in inaccuracies. For example, use of a pupil location can result in height determination errors since pitching the head back raises the eye location and could compensate for a non-alignment of the back. The result would be a lower heart height but no indication that the subject was in the wrong location.

Figure 27:
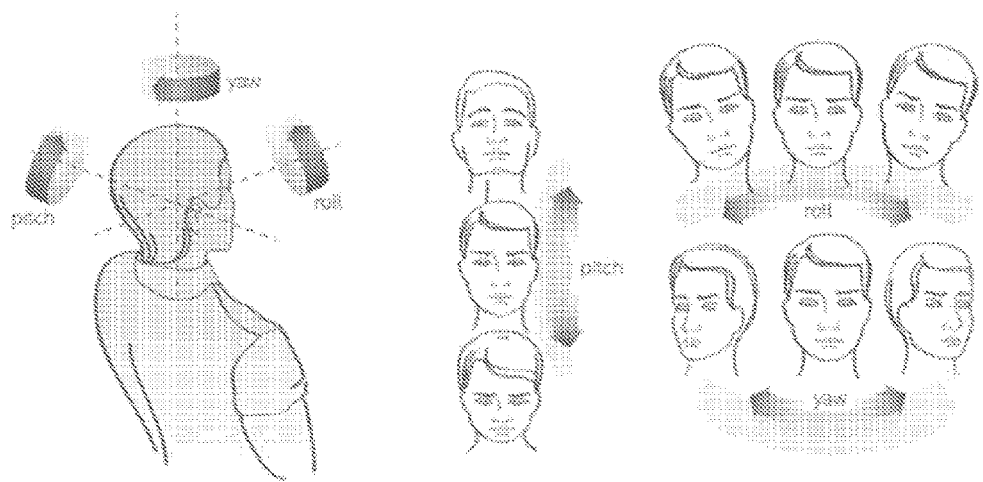
FIG. 27 illustrates determination of the roll, pitch, and yaw of the head.

The head position determination system uses a camera with 3-D capabilities such that head roll, pitch, and yaw are determined. FIG. 27 shows these elements as calculated for a depth camera. Note, a non-depth camera can be used but overall accuracy of the system can be better using a depth camera. The camera is located so as to capture the face of the subject as well as the upper torso. The camera provides the head position information and can provide additional information regarding neck, chest and shoulder position.

In use, the subject can define a maximum head position that is comfortable and sustainable for the measurement duration. This head position becomes the datum upon which other measurements are compared. For future measurements, the subject places their arm in the enclosure and sits on the same chair. Using visual feedback tools, the subject is instructed to reposition their head in a manner consistent with the prior datum. The result is a repeatable heart height.

In practice, some subjects might have difficulty satisfying the position repeatability criteria due to small change in body position of head alignment. This can be addressed by obtaining multiple measurements within a brief period of time to map out these possible variances in position. The method can also use additional information to facilitate the repositioning of the subject. For example, the relationship between the neck and torso can also be determined and used to facilitate repositioning. This method has similarities to the volume assessment approach but is based upon alignment angles, which are less sensitive to clothing differences.

Some subjects (typically older subjects) have significant kyphosis, also known as roundback or hunchback. In the presence of such a condition, both methods continue to create a repeatable positioning mechanism for central venous pressure measurements.

Other optical methods can include the use of one or more (e.g., three) optical markers such as IR reflectors on the body. The optical markers can be configured in one device such that the position relative to the camera can be determined as can the angle of the reflector on the chest. Additional approaches can include the placement of markers on the upper body other areas to include the head.

Non-optical systems can include the use of a manometer and inertial measurement unit (IMU). A flexible U-shaped manometer provides the relative height between the two ends of the tube due to the difference in hydrostatic pressure between the ends. One end of the manometer is attached to the body using an external landmark, (e.g. sternal notch) and the other end is vertically aligned with the location of the peripheral vein. The manometer measures the vertical distance between peripheral vein location and the reference point. Since heart is inside the chest, it is important to consider the angle of the upper body. The IMU can be used to determine the angle of the torso. The resulting information can be used to generate a repeatable body position, or to compensate for a change in body position relative to prior measurements.

A combination system using a camera and IMU attached to an external landmark can also be used to determine heart height. The resulting information from both the camera and IMU can be combined to measure position and orientation.

EXAMPLE EMBODIMENTS

Vein Imaging with Controlled Arm Raise

A system and method utilizing a controlled arm raise can be implemented in various ways, the following is an illustration of one example embodiment. FIG. 28 shows the combined use of a venous imaging system and a 3-dimensional imaging system for making anatomical measurements. As the subject approaches the system and sits down in FIG. 28A, a forward-facing camera 1201 is used to capture the anatomical dimensions and landmarks of the subject. The optical system 1202 images the tissue in a manner that enables venous volume determination. The system can then acquire images while raising the arm in a defined and controlled manner. FIG. 28B shows the arm being raised to the point above central venous pressure.

Figure 29:
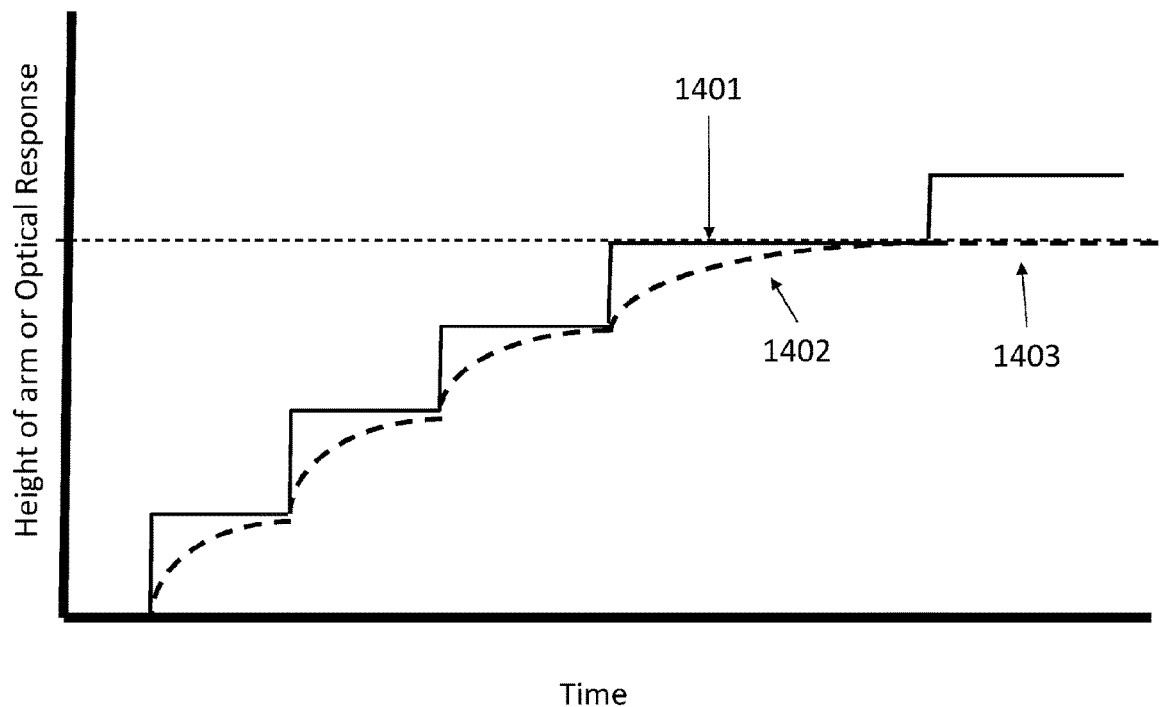
FIG. 29 is an illustration of a measurement protocol for minimizing the impact of time delays.

The use of a controlled arm motion helps to mitigate the impact of physiological delays in the response of the system. In one use scenario, the system can raise the arm in a series of small discrete steps, waiting for equilibration of the optical response before proceeding to the next position. FIG. 29 illustrates such an arm raise protocol. Beyond the point where transmural pressure is zero, additional height increases can result in minimal additional venous volume changes. The equilibration of venous volume prior to movement is important since it allows one to remove the influence of response delays. The increment of height change can be constant, or can vary to optimize sampling of the pressure-volume curve, with more samples in regions of large change. Thus, the height increment can be dependent on the response characteristics to the prior position change. If the previous response change is large, the height increment can be reduced, and if it is small, the height increment can be increased. FIG. 29 is an illustrative example of the above method. As a hydrostatic pressure approaches central venous pressure 1401, the overall time of equilibration increases 1402. At the height where hydrostatic pressure equals central venous pressure, 1403, no additional venous compression will transpire with additional arm elevation. This type of systematic approach minimizes the impact of system delays in the determination of an accurate central venous pressure.

FIG. 30 shows example data from a vein imaging system embodiment during a controlled arm raise. Images of the dorsal hand veins were acquired using an infrared camera and illumination at 805 nm. In the images, veins appear as darker regions because the blood is a large absorber of infrared light. FIG. 30A shows a sequence of images taken at successively higher hand heights. The absorbance difference due to vein collapse is apparent: the dark vein regions nearly disappear at the higher positions. FIG. 30B shows the time course of the hand height and image intensity over the controlled arm raise. The intensity is determined from within the "venous mask" which is created using a binary segmentation of the initial image. During the experiment, the arm was raised using a rotational stage, as illustrated in FIG. 28. The arm was raised in constant increments only after the intensity signal had equilibrated to the last height change. Examination of the plot shows that around −5 cm (relative to the suprasternal notch), height changes caused large changes in the optical signal due venous collapse. The steady-state (after equilibration) values of intensity are shown as a function of height in FIG. 30C. Based on the change in optical signal as a function of height, it is apparent that venous collapse has occurred by 3 cm.

As one of skill in the art can appreciate, there are many alternative methods that can be used to analyze to vein imaging data, including decomposition methods, measurement of vein width, and region-of-interest approaches.

Wrist-Based Device with Controlled Arm Raise

Figure 31:
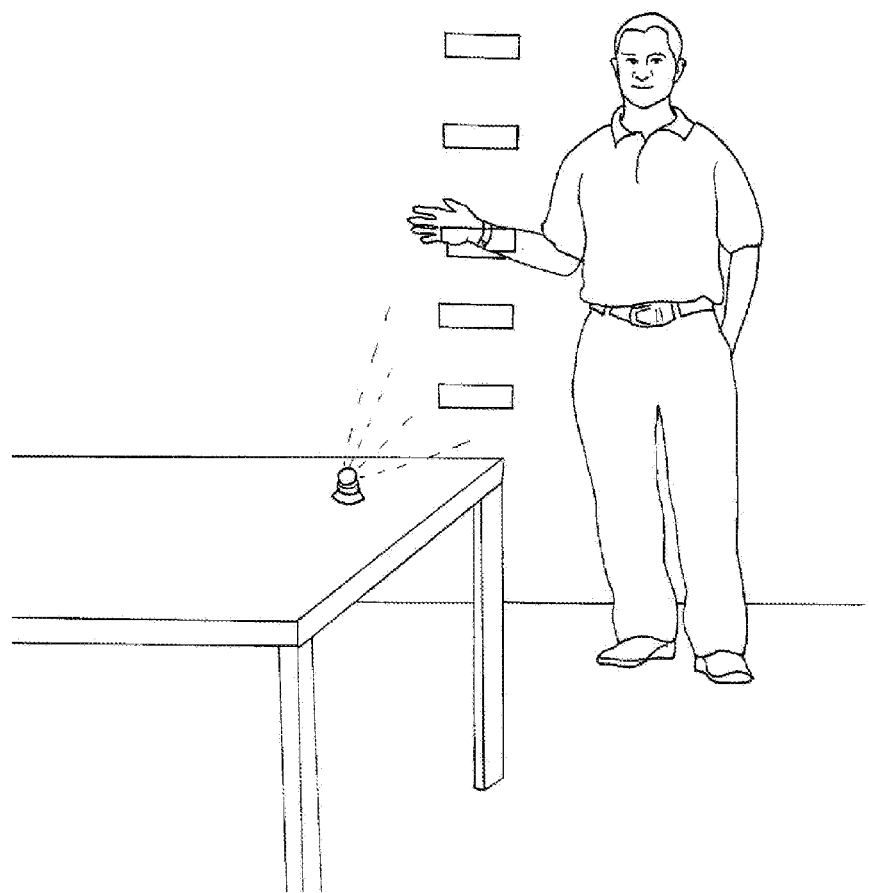
FIG. 31 is an illustration of a subject initiated arm movement.

A controlled arm raise can also be implemented with subject-initiated movement. In one scenario, a wrist-based optical assessment system, e.g., a watch band as described previously, can be combined with a remote projection system that displays the positions to which the user must move their hand. Such a system is illustrated in FIG. 31. The subject can be informed to raise their hand to the next displayed target only after receiving a visual or auditory cue. The projection system can use a camera to determine the distance to the wall (or other projection surface) and to ensure that the subject has moved appropriately. Alternatively, photo-detectors on the watch band can be used to determine that the subject had raised their hand to the appropriate location. Visual feedback as well as audio feedback can be provided to the subject to indicate appropriate movement and positioning. The wrist system can communicate with the projection system through wireless or BLUETOOTH connectivity.

Figure 32:
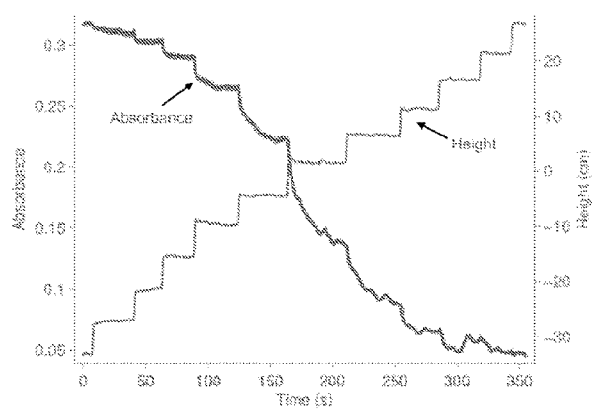
FIG. 32 is an example of wrist-based optical data during a subject-initiated arm movement.
Figure 32:
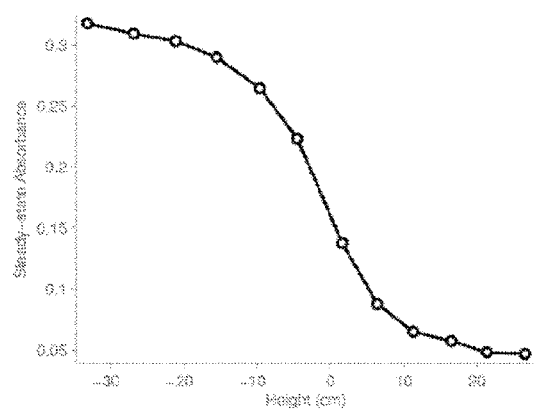

FIG. 32 is an example of data collected from a PPG wrist-based sensor during user-initiated arm movement. Visual targets were displayed at even height increments, and the user was cued to move only after the PPG signal had reached a roughly steady-state value. The time courses of optical absorbance and wrist height are shown in FIG. 32A, while the steady-state absorbance as a function of height is shown in FIG. 32B. Inspection of the graph shows venous collapse prior to 5 cm above the suprasternal notch.

Noncontact Dynamic Pressure Tonometer

Figure 33A:
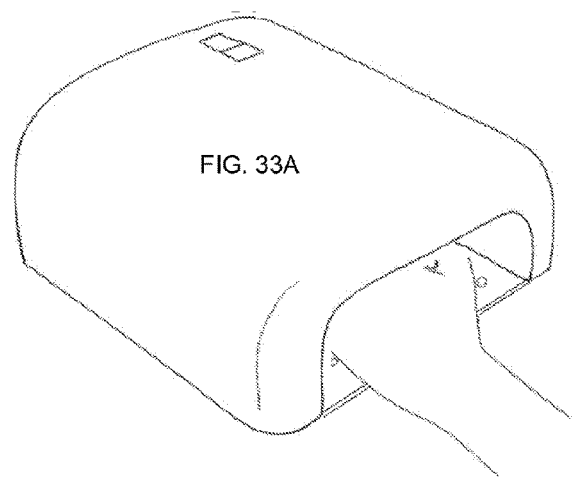
FIG. 33 is an illustration of a central venous pressure measurement system utilizing dynamic air pressure.
Figure 33B:
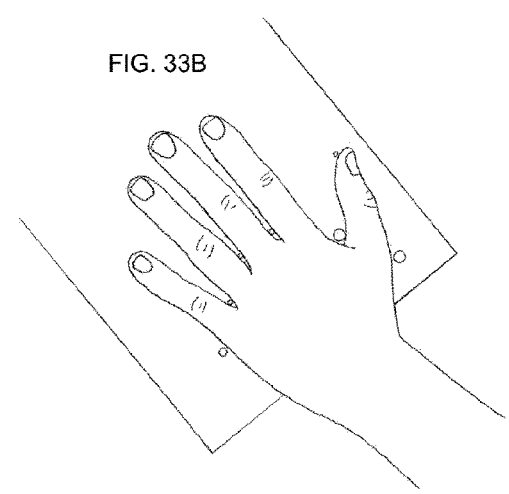
Figure 33C:
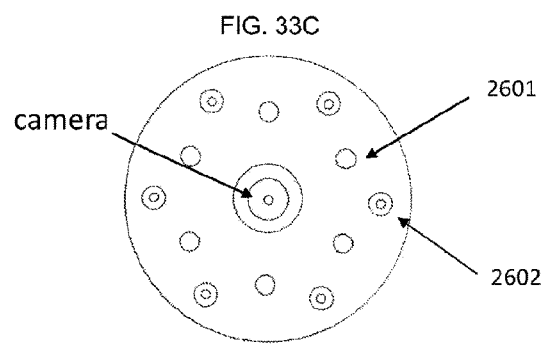

FIG. 33A is an illustration of a central venous pressure measurement system embodiment that utilizes dynamic (velocity) pressure for the determination of venous collapse. Dynamic pressure is the result of changes in direction and velocity of air flow. The system does not require the subject to move their hand, but rather changes the external force on the tissue in a manner that results in a systematic change in transmural pressure. In operation, the system can use a vein imaging system for isolation of a one or more measurement sites within the area affected by the controlled airstream. Such a methodology minimizes the impact of autonomic changes resulting from arm elevation. The noncontact tonometer system can include a 3D camera to evaluate the subject's heart height relative to the system. The actual measurement of venous volume can be determined by examination of absorbance changes as measured from the vessel, height changes if the optical system is aligned to the side for vein height determination, and vessel dimension changes. To facilitate repeatable measurements, the system can include a finger alignment system in the form of alignment pegs, as shown in FIG. 33B. The device for illumination, image capture and air management is illustrated in FIG. 33C. Illumination of the hand is done by optical sources 2601 with air directed by 2602. The system can also enable transmission illumination by placement of light sources below the hand.

FIG. 34 demonstrates changes in venous volume achieved by modulations in applied air pressure. During this example measurement, infrared images of the dorsal hand veins were acquired while air flow was directed onto the surface of the hand. Air flow velocity was modulated in a binary fashion between low and high states with a period of approximately 20 seconds. FIG. 34A shows image frames from the example measurement at times of minimal and maximal flow. Examination of the sequence of images shows repeatable changes in venous volume as a function of the air flow. Veins are wider and darker during minimal air flow periods than during maximal air flow periods. FIG. 34B shows the average optical signal intensity inside a venous mask, created using binary segmentation of the initial image. The time course of venous collapse induced by the air pressure is plainly visible. The frames displayed in FIG. 34A are denoted with circles for minimal flow and squares for maximal flow. FIG. 34C displays the average pixel intensities for a cross-section through the image at times of maximal and minimal flow. The cross-section is indicated in the first panel of FIG. 34A. The width of the primary vein (centered roughly at pixel 70) can be seen to shrink considerably when maximal flow is applied. Thus, noncontact pressure modulations with air flow result in substantial optical signal changes that can be analyzed both in terms of changes in intensity magnitude and changes in spatial and morphological properties.

Noncontact Static Pressure Tonometer

Figure 35:
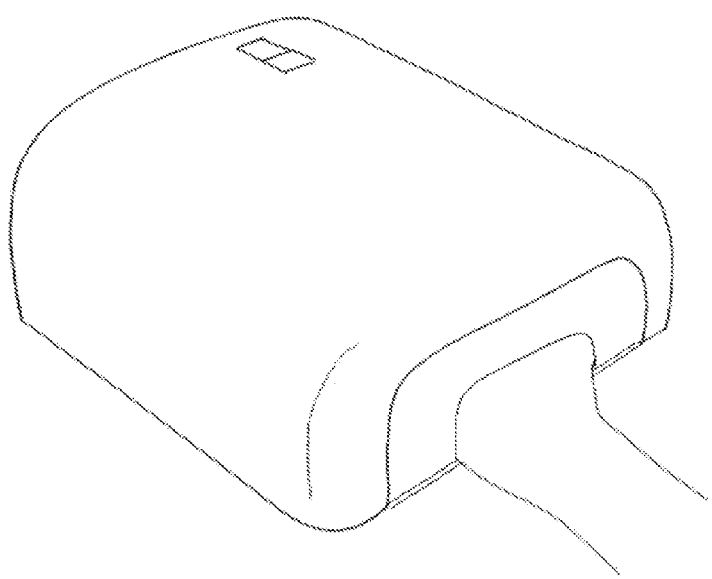
FIG. 35 is an illustration of central venous pressure measurement system using static air pressure.

The system can use a static or mostly static pressure mechanism for changing transmural pressure. The system operates by having the user place their hand into an enclosure through an entry port or aperture. The box has an entrance port that is sized to allow the hand to enter the box, but concurrently minimizes residual space around the wrist. FIG. 35 illustrates such a design. In some embodiments, the space around the wrist can be minimized by multiple mechanisms including as an example an iris diaphragm. Iris diaphragms are commonly used in optical system to close a circular opening in a systematic manner. The mechanism used for creating a seal around the wrist should not impede venous flow from the hand in a manner that creates CVP measurement error. Suitable mechanisms are described in PCT patent application PCT/US17/62356, filed 17 Nov. 2017, which is incorporated by reference. Measurement error can be reduced by using a system that does not contact the wrist, contacts only non-venous tissues in the wrist, or contacts the wrist with a pressure that is below typical venous pressures. FIG. 35 illustrates that the subject's wrist can rest on a table or other surface as it enters the enclosure. In the distal forearm, the primary superficial conduits for venous flow are the basilic and cephalic vein, which follow the medial and lateral aspects of the forearm, respectively. Thus, the volar surface of the distal forearm is free of major veins and contact pressures can be applied to this surface without affecting the CVP measurement.

Central Venous Pressure can be determined by altering the pressure in the box such that transmural pressure is changed in a measurable manner. If the volume of air being pushed into the box exceeds the volume exiting the box, then the pressure in the box will increase, decreasing the transmural pressure across the venous compartment. During operation, the subject is not required to move their hand; all changes in transmural pressure are mediated by changes in air pressure. In one embodiment, the system can use a vein imaging system for isolation of a one or more measurement sites within the area imaged by the system. To ensure accurate measurements, the external part of the system can include a 3D camera or simple U-tube manometer to evaluate the subject's heart height relative to the system. The actual measurement of venous volume can be determined by examination of absorbance changes as measured from the vessel, height changes if the optical system is aligned to the side for vein height determination, and vessel dimension changes. To facilitate repeatable measurements, the system can include a finger or hand alignment system. Note that the system can also create a below atmospheric pressure, thus facilitating venous pooling in the site. Such a capability might be of value for defining a standardized initial conditions for the test. In practice, a decrease in pressure below atmospheric pressure can be used and a stable venous volume signal determined before starting the test. Alternatively, a high pressure condition can be used as an initial condition to ensure minimal venous volume. In another approach, starting conditions can utilize periodic pressure modulations to exhaust venous stretch receptors and precondition the veins for further perturbations. Such defined initial conditions can be used to improve measurement accuracy.

Figure 36:
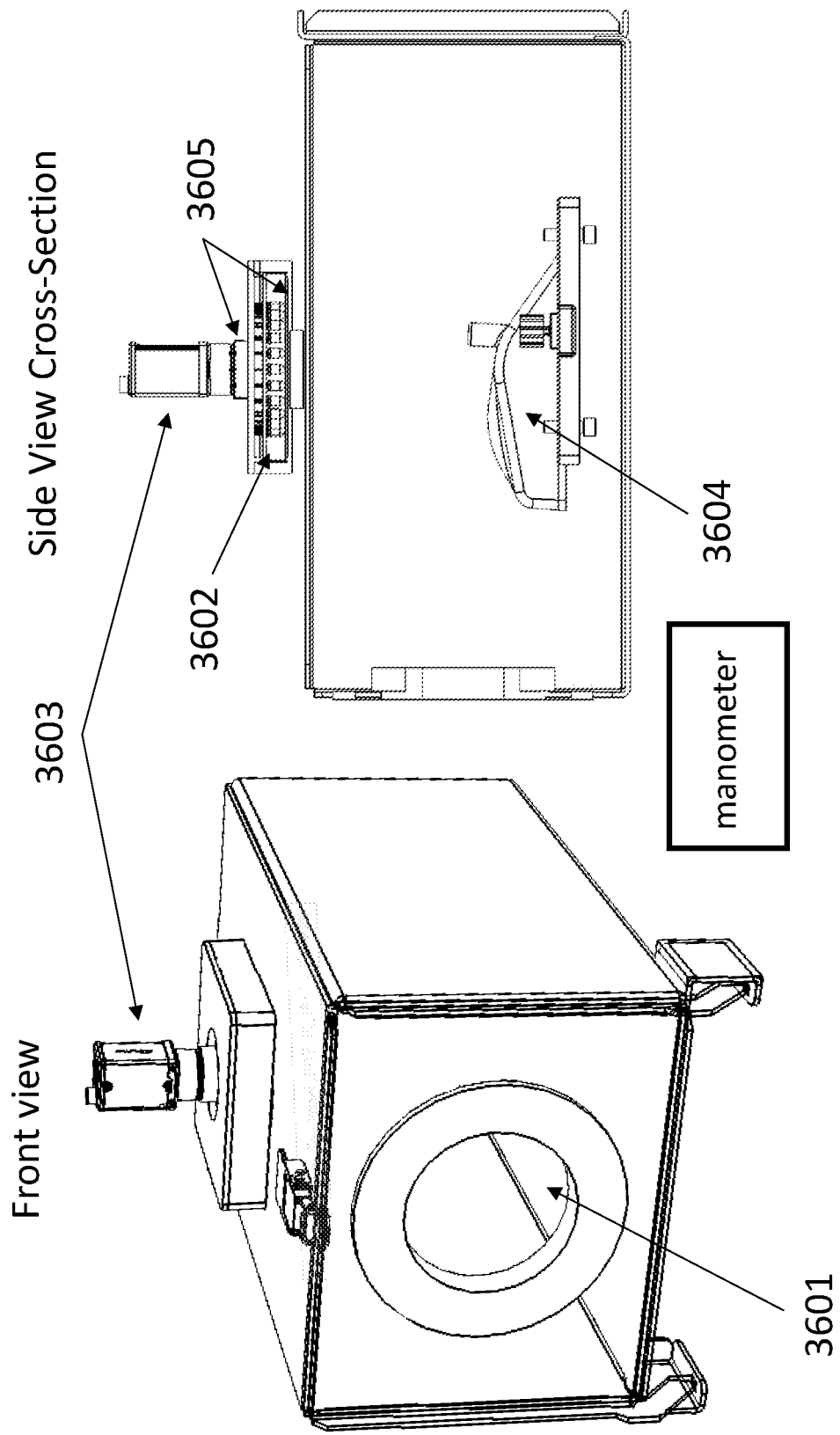
FIG. 36 is a schematic of a central venous pressure measurement system using static air pressure.

FIG. 36 shows an example of a central venous pressure measurement system using static air pressure to change transmural pressure and a camera to detect changes in venous volume. The hand is placed in a box through an aperture, 3601, sized to the subject's wrist and a flexible silicone sleeve (not shown). The sleeve enables creation of a pressure seal that does not create contact pressures exceeding the pressure in the box. The air pressure inside the box can be changed by using a centrifugal blower at an air inlet (not shown) and a butterfly valve at the outlet (not shown). Rotation of butterfly valve permits or restricts the air flow. The desired box pressure can be set via custom software and a pressure sensor recording pressure inside the box can be coupled with a PID controller to adjust the position of the butterfly valve to reach the target pressure. The hand is rested on a palm rest, 3604, which provides static friction opposing the force of the enclosure pressure. The hand is illuminated from above by a ring of LEDs, 3602, with a center wavelength of 850 nm. An infrared-sensitive monochrome camera, 3603, captures digital images of the dorsal surface of the hand. Reflectance illumination enhances specificity to dorsal hand veins and minimizes contributions of deeper veins and arterial sources to the optical signal. Orthogonally oriented linear polarizers, 3605, are placed below the LEDs and in front of the camera lens and are used to reduce specular reflections. A manometer is used to determine the vertical distance between the right atrium and the dorsal hand. One end of the manometer is attached to the phlebostatic axis (located at the fourth intercostal space at the mid-anterior-posterior diameter of the chest wall) and the other end is attached to the box at the location of the hand. This measurement is used to account for the effect of hydrostatic pressure.

FIG. 37 demonstrates a method by which central venous pressure can be determined using the system FIG. 36. Images of the dorsal hand veins are captured with the infrared camera, as shown in FIG. 37A. As shown in FIG. 37B, a pressure profile combining a linear ramp with square modulations is used to change the transmural pressure. The modulation amplitude is kept relatively small (4 cmH2O) to avoid protracted venous filling times. Images undergo frame-by-frame registration to accommodate movements or distortion introduced by the subject or induced by the pressure change. Image analysis identifies venous clusters, 3701, shown in FIG. 37C based on variance associated with the pressure profile and local neighborhood statistics. The intensity signals from venous pixels are transformed to relative absorbances and undergo temporal high pass filtering to remove low frequency noise sources. A Savitzky-Golay filter is also applied to remove the influence of heart rate without overly blurring temporal features. FIG. 37D shows the processed mean venous signal. The period over which transmural pressure traverses zero can easily be identified as that causing the largest modulation in the venous absorbance. A pressure vs. modulation relationship can be constructed by considering the average pressure over a window and calculating the associated change in absorbance. Curves for each venous cluster, determined using a local smoothing algorithm, are shown in FIG. 37E. The curves can be compared to confirm relative spatial homogeneity across different venous segments. If this condition is met, the peripheral venous collapse pressure can be estimated from the peak of the pressure vs. modulation curve, 3702, as shown in FIG. 37F. In this example, the peripheral pressure is identified as 21.3 cmH2O. The vertical distance between the dorsal hand and the phlebostatic axis added 17.2 cmH2O of hydrostatic pressure, as determined with the manometer. The CVP was thus determined as 4.1 cmH2O, after subtracting the hydrostatic pressure from the peripheral venous pressure. These analysis steps represent only one example of how central venous pressure can be determined, and that many alternative approaches to image and signal processing can be used to extract similar information.

FIG. 38 demonstrates sensitivity of the method to changes in peripheral venous pressure. In a set of experiments performed on a single subject, the peripheral venous pressure was manipulated by changing the height of the hand relative to the heart and therefore changing the hydrostatic pressure in the hand veins. FIG. 38A shows the pressure vs. modulation curve for the starting location of the hand, while FIG. 38B shows the curve when the hand is lowered. Lowering the hand increases the hydrostatic pressure in the veins and shifts the collapse point (zero transmural pressure) to the right. As shown in FIG. 38C, repeating the experiment over several hand positions demonstrates that the peripheral venous pressure (PVP) has a consistent and highly reproducible relationship with the hydrostatic pressure (HSP). Thus, the central venous pressure can be determined as CVP=PVP−HSP regardless of the hand height.

Air Pressure Cuff

Another example embodiment of a static and dynamic pressure system uses air pressure to create an air cuff at the wrist. The ability to systematically change the transmural pressure at a location between the capillary and the heart creates several measurement options. Specifically, the ability to create a controlled venous return mechanism enables manipulation of intravascular pressures for the measurement of central venous pressure.

As one of skill in the art can appreciate, many alternative embodiments exist for using air flows, air pressure, or combinations of the two to create extravascular and intravascular transmural pressure changes for the determination of CVP.

Optical Tonometer

Figure 39:
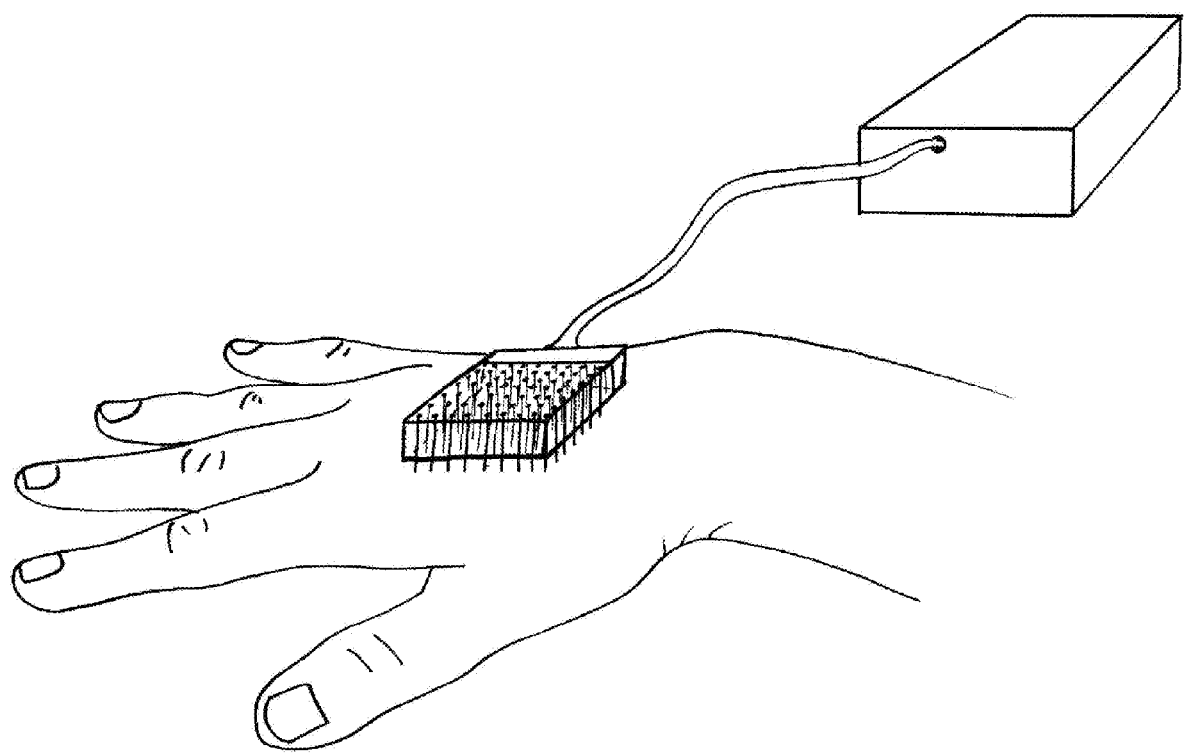
FIG. 39 is an illustration of an optical tonometer example embodiment.

An optical tonometer example embodiment is based upon the use of one or more optical fibers that can be placed in contact with the tissue. The optical fiber can interact with the tissue in a predefined manner such that different levels of force can be applied to the tissue. The mechanism of force application to the tissue is via the optical fiber, which also represents the measurement modality. The optical fiber can measure the absorbance change with increasing pressure due to the pressure exerted by the fiber. The pressure point where no additional change in absorbance has occurred or a maximum transition has occurred, enables determination of venous collapse and zero transmural pressure. The resulting force needed to obtain the zero-transmural pressure point in combination with the height of the hand relative to the heart enables central venous pressure determination. For the purposes of creating a self-administered test, a distributed array of optical fibers can be utilized much like the child's toy that utilizes multiple pins to effectively conform to the surface of the hand. The resulting array of fiber optics can be transmitted back to an imaging spectrometer for evaluation. FIG. 39 is an illustration of the optical tonometer example embodiment.

The present invention has been described in connection with various example embodiments. It will be understood that the above description is merely illustrative of the applications of the principles of the present invention, the scope of which is to be determined by the claims viewed in light of the specification. Other variants and modifications of the invention will be apparent to those skilled in the art.

The invention claimed is:

1. An apparatus for determining central venous pressure of an individual comprising:
   (a) a pressure mechanism to vary transmural pressure in the veins of a limb of the individual;
   (b) an optical measurement system responsive to blood presence in a measurement region of the limb and configured to determine a measure of blood volume at each of a plurality of transmural pressures;
   (c) a height determination device that determines the height of the measurement region relative to an anatomical reference point;
   (d) an analysis system configured to determine central venous pressure from the determined height and from the relationship between transmural pressure and blood volume.

2. An apparatus as in claim 1, wherein the analysis system is configured to determine central venous pressure from the determined height and from the transmural pressure at which the determined measure of blood volume indicates transmural pressure has reached zero.

3. An apparatus as in claim 1, wherein the pressure mechanism comprises a mechanism to vary the external pressure on the veins.

4. An apparatus as in claim 3 wherein the pressure mechanism comprises
   (a) a pressurizable enclosure, having a sealing mechanism configured to surround a first portion of the limb and configured to apply a pressure to the veins in the first portion of the limb that is greater than the pressure on a second portion of the limb not surrounded by the enclosure;
   (b) a control mechanism configured to apply a plurality of pressures to the veins.

5. An apparatus as in claim 4, wherein the sealing mechanism comprises a seal that engages using the applied pressure.

6. An apparatus as in claim 5, wherein the control system applies a plurality of pressures to the veins by varying the rate of air flow exiting the enclosure.

7. An apparatus as in claim 4, wherein the control system is configured to apply to the veins a plurality of pressures that increase over time.

8. An apparatus as in claim 4, wherein the control system is configured to apply to the veins a pressure that is modulated over time.

9. An apparatus as in claim 8, wherein the modulated pressure has a frequency between 1 Hz and 0.05 Hz.

10. An apparatus as in claim 8, wherein the modulated pressure has a modulation amplitude less than 10 cmH2O.

11. An apparatus as in claim 4, wherein the control system is configured to apply to the veins a plurality of pressures that change in discrete increments over time.

12. An apparatus as in claim 1, wherein the optical measurement system comprises:
   (a) an illumination system configured to direct light to the veins, where the light includes one or more wavelengths that are absorbed by deoxygenated hemoglobin;
   (b) an optical sensing device that is sensitive to the one or more wavelengths.

13. An apparatus as in claim 12, wherein the optical sensing device is configured to collect light reflected from the tissue in the limb.

14. An apparatus as in claim 13, further comprising first and second polarizers configured to discourage spectrally reflected light from reaching the optical sensing device.

15. An apparatus as in claim 13, wherein the optical sensing device is further configured to collect light transmitted through the tissue in the limb.

16. An apparatus as in claim 12, wherein the optical sensing device is configured to collect light transmitted through the tissue in the limb.

17. An apparatus as in claim 1, wherein the optical measurement system captures an image of the veins.

18. An apparatus as in claim 17, wherein the analysis system is configured to determine from an image of the veins the size, volume, or blood content of the veins.

19. An apparatus as in claim 1, wherein the height determination device comprises a manometer.

20. An apparatus as in claim 1, wherein the height determination device comprises an imaging system, separate from the optical measurement system.

21. An apparatus as in claim 20, wherein the imaging system is configured to determine anatomical dimensions of the individual.

22. An apparatus as in claim 20, wherein the imaging system is configured to determine the location of a volume of the individual's body in space.

23. An apparatus as in claim 20, wherein the imaging system is configured to determine the position of the individual's head.

24. An apparatus as in claim 1, wherein the optical measurement system is configured to apply no contact pressure to the region of the limb.

25. An apparatus as in claim 1, wherein the optical measurement system is configured to measure a region of the limb where a venous blood signal is dominant over an arterial blood signal.

* * * * *